(12) United States Patent
Liu

(10) Patent No.: US 9,719,130 B2
(45) Date of Patent: *Aug. 1, 2017

(54) SAMPLE COLLECTION DEVICES, KITS AND METHODS OF USE

(71) Applicant: LIFE TECHNOLOGIES CORPORATION, Carlsbad, CA (US)

(72) Inventor: Jason Yingjie Liu, Foster City, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 362 days.

This patent is subject to a terminal disclaimer.

(21) Appl. No.: 14/380,543

(22) PCT Filed: Feb. 22, 2013

(86) PCT No.: PCT/US2013/027417
§ 371 (c)(1),
(2) Date: Aug. 22, 2014

(87) PCT Pub. No.: WO2013/126765
PCT Pub. Date: Aug. 29, 2013

(65) Prior Publication Data
US 2015/0024400 A1 Jan. 22, 2015

Related U.S. Application Data

(60) Provisional application No. 61/601,901, filed on Feb. 22, 2012, provisional application No. 61/724,782, filed on Nov. 9, 2012.

(51) Int. Cl.
*C12Q 1/68* (2006.01)
*G01N 1/30* (2006.01)
*A61B 10/00* (2006.01)
*A61B 10/02* (2006.01)

(52) U.S. Cl.
CPC ........ *C12Q 1/6806* (2013.01); *A61B 10/0045* (2013.01); *A61B 10/02* (2013.01); *G01N 1/30* (2013.01)

(58) Field of Classification Search
CPC .. A61B 10/0045; A61B 10/02; C12Q 1/6806; G01N 1/30
See application file for complete search history.

(56) References Cited

U.S. PATENT DOCUMENTS

| | | |
|---|---|---|
| 4,190,056 A | 2/1980 | Tapper et al. |
| 5,876,926 A | 3/1999 | Beecham |
| 6,229,908 B1 | 5/2001 | Edmonds et al. |
| 6,643,531 B1 | 11/2003 | Katarow |
| 7,308,123 B2 | 12/2007 | Fenrich et al. |
| 8,041,084 B2 | 10/2011 | Fenrich et al. |
| 8,307,854 B1 | 11/2012 | Vu et al. |
| 8,792,687 B2 | 7/2014 | Baughman et al. |
| 9,058,646 B2 | 6/2015 | Harrold et al. |
| 2002/0183624 A1 | 12/2002 | Rowe et al. |
| 2004/0143196 A1 | 7/2004 | Chen |
| 2006/0074280 A1 | 4/2006 | Martis et al. |
| 2006/0131391 A1 | 6/2006 | Penuela |
| 2007/0076923 A1 | 4/2007 | Chiu et al. |
| 2007/0249961 A1 | 10/2007 | Davin et al. |
| 2008/0194041 A1 | 8/2008 | Guirguis |
| 2009/0227897 A1 | 9/2009 | Wendt et al. |
| 2009/0257626 A1 | 10/2009 | Sherlock et al. |
| 2010/0030111 A1 | 2/2010 | Perriere et al. |
| 2010/0041131 A1 | 2/2010 | Brown |
| 2010/0098831 A1 | 4/2010 | Anderson et al. |
| 2010/0184126 A1 | 7/2010 | Rutty et al. |
| 2010/0191147 A1 | 7/2010 | Miyoshi et al. |
| 2011/0163163 A1 | 7/2011 | Rowe |
| 2011/0172510 A1 | 7/2011 | Chickering et al. |
| 2012/0103421 A1 | 5/2012 | Grenz et al. |
| 2012/0165697 A1 | 6/2012 | Kelly et al. |
| 2013/0078625 A1 | 3/2013 | Holmes et al. |
| 2013/0101184 A1 | 4/2013 | Harrold et al. |
| 2013/0106568 A1 | 5/2013 | Harrold et al. |
| 2013/0202182 A1 | 8/2013 | Rowe |
| 2016/0154990 A1 | 6/2016 | Harrold et al. |

FOREIGN PATENT DOCUMENTS

| | | |
|---|---|---|
| DE | 202005020535 U1 | 5/2006 |
| EP | 1504722 A2 | 2/2005 |
| WO | 9907282 A1 | 2/1999 |
| WO | 2006061771 A2 | 6/2006 |

(Continued)

OTHER PUBLICATIONS

Wang, Y. et al., "Data Acquisition and Quality Analysis of 3-Demensional Fingerprints", Florida: IEEE conference on Biometrics, Identity and Security. http://vis.uky.edu/~realtime3d/Doc/3D_Fingerprint_Quality.pdf, Retrieved Mar. 2000, 10 pages.

(Continued)

*Primary Examiner* — Cynthia B Wilder
(74) *Attorney, Agent, or Firm* — Priya D. Subramony; Peter G. Foiles

(57) ABSTRACT

Devices, methods, and kits are disclosed for collection, labeling and analysis of samples containing a substance of interest. Such devices and methods are used in forensic, human identification, access and importation control, and other investigative technologies to collect even limited amounts of a substance of interest that may be present on a substrate and to facilitate analysis to identify the substance of interest.

13 Claims, 15 Drawing Sheets

(56) References Cited

FOREIGN PATENT DOCUMENTS

| WO | 2007120865 A2 | 10/2007 |
| WO | 2009018473 A1 | 2/2009 |
| WO | 2009021130 A1 | 2/2009 |
| WO | 2011026169 A1 | 3/2011 |

OTHER PUBLICATIONS

Wang, Y. et al., "Fit-sphere unwrapping and performance analysis of 3D fingerprints", Optical Society of America, vol. 49, Feb. 1, 2010, pp. 592-600.

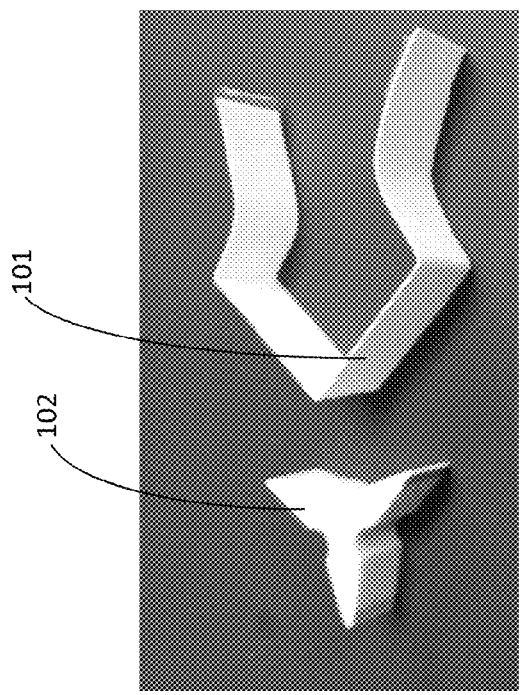
FIG 1A-1
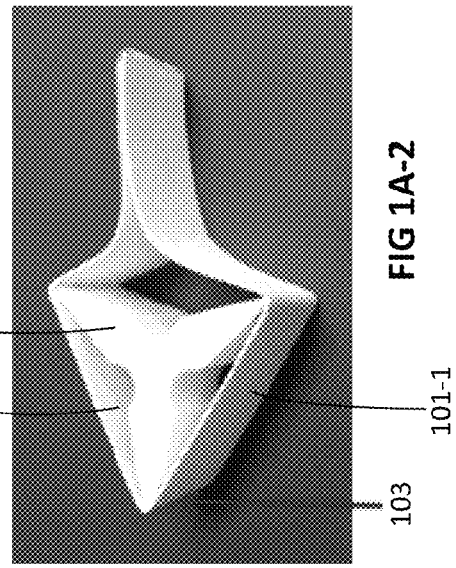
FIG 1A-2
FIG 1A

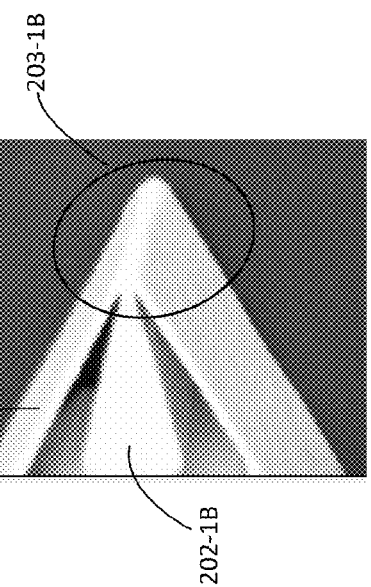
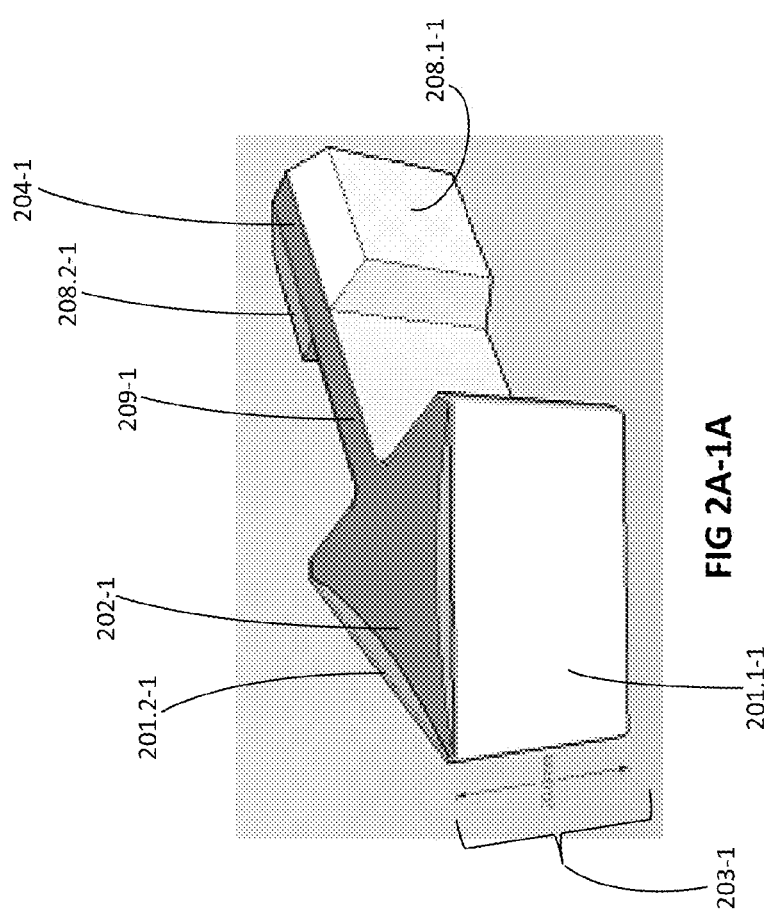
FIG 2A-1B
FIG 2A-1A
FIG 2A

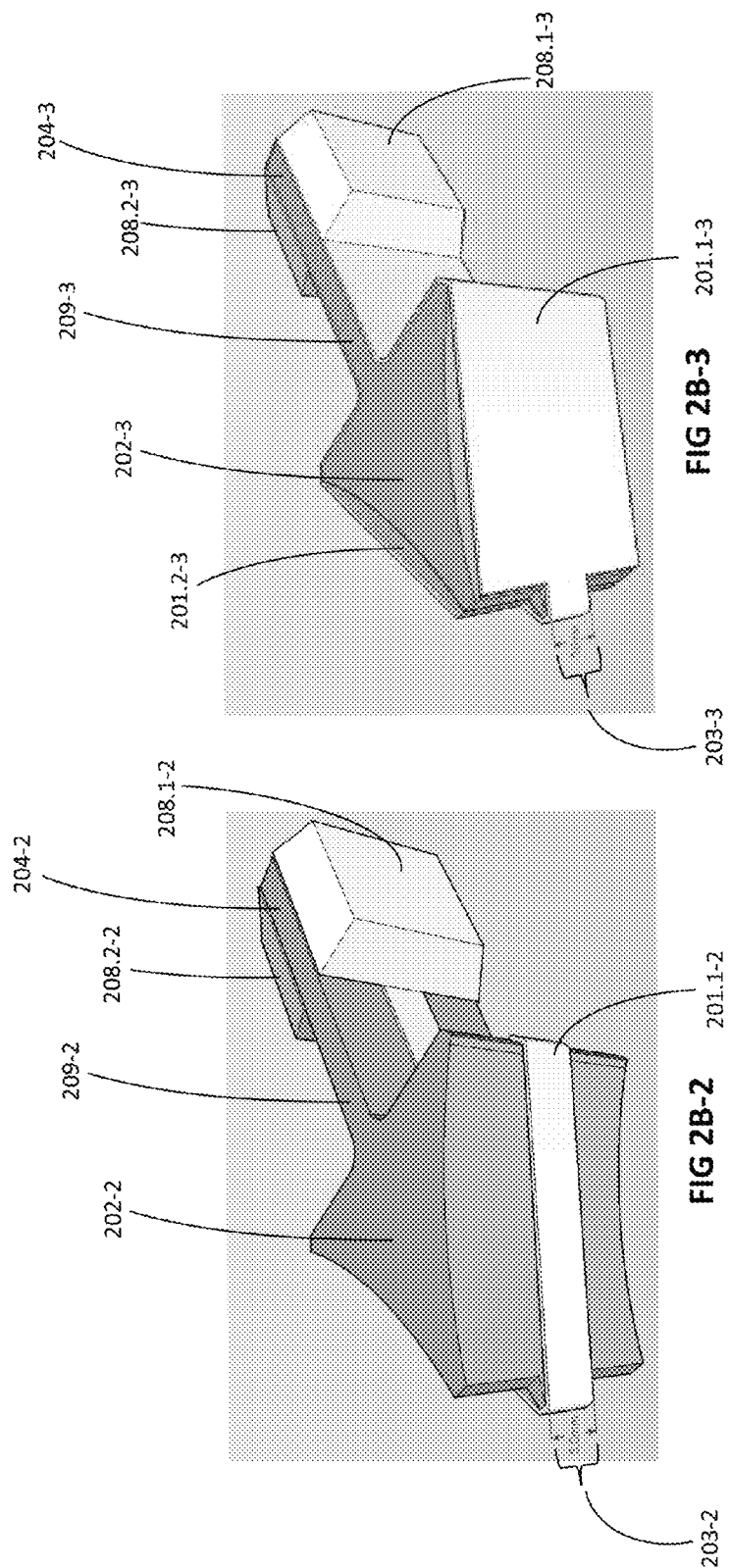

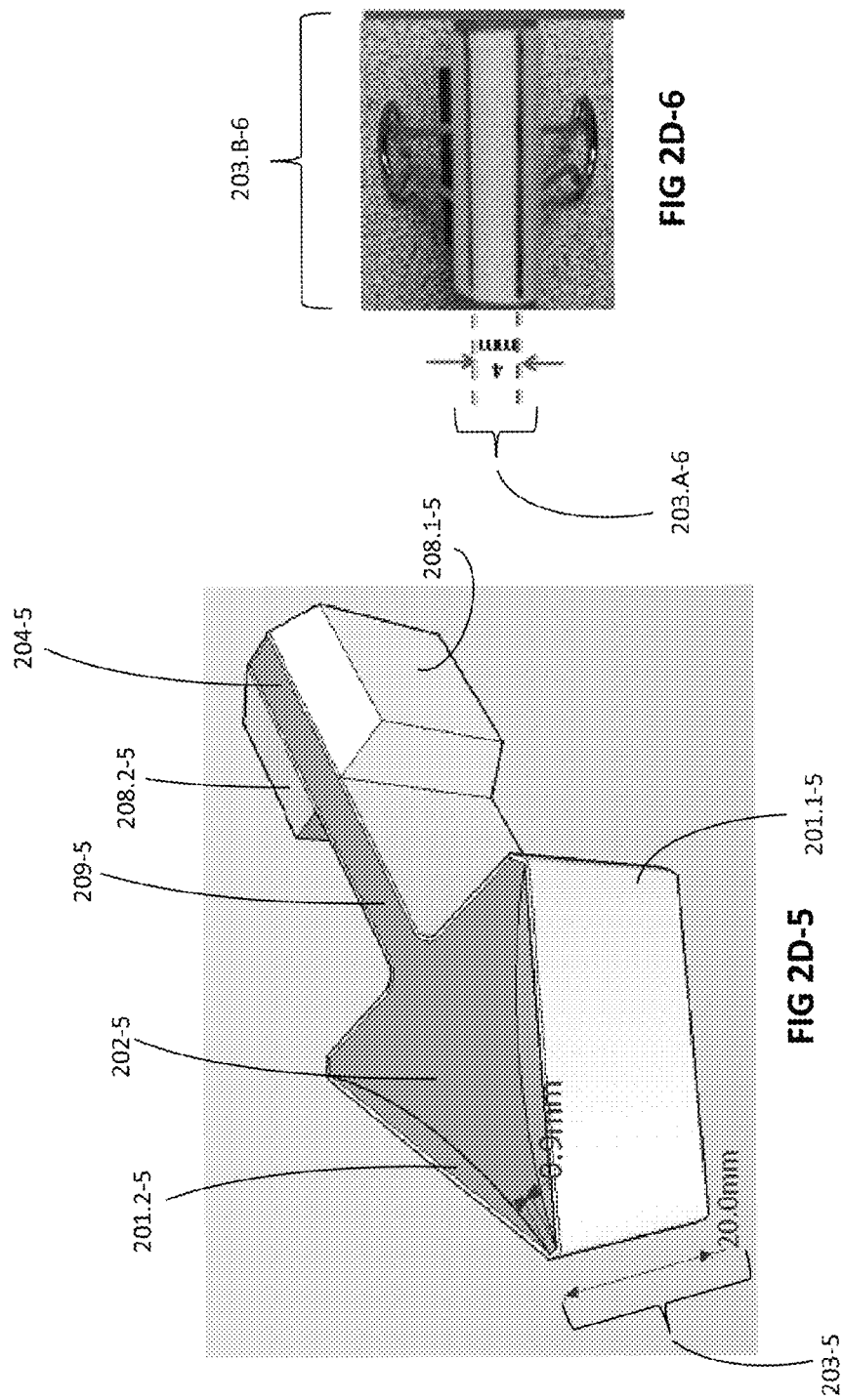

SAMPLE COLLECTION DEVICES, KITS AND METHODS OF USE

This application is the National Stage of International Application No. PCT/US2013/027417 filed on Feb. 22, 2013, which International Application claims the benefit of priority under 35 U.S.C. §119(e) to U.S. Provisional Application No. 61/601,901 filed on Feb. 22, 2012, and to U. S. Provisional Application No. 61/724,782 filed on Nov. 9, 2012, each disclosure of which is incorporated by reference in its entirety.

The section headings used herein are for organizational purposes only and should not be construed as limiting the subject matter described herein in any way.

FIELD

The present teachings relate to devices and methods for obtaining biological, environmental, and/or chemical samples for use in a variety of identification modalities, including human identification, animal identification, pathogen identification, forensics identification, and environmental analyses.

INTRODUCTION

Forensic evidence, environmental samples, and samples including biological material used for identification of humans, animals, plants, pathogens, and chemical signatures of substances of interest are often present in very limited amounts, thereby complicating collection and subsequent testing. Therefore, there remains a need to accurately collect and be capable of processing samples to provide identification of one or more substances that may be of interest within the sample.

SUMMARY

In a first aspect, the invention provides a sample collection device including an active collection component having a first surface area configured to be an active collection surface area; a handling component; where the active collection component is detachably connected to at least one of a first or a second portion of the handling component; and where the device is configured to: a) collect a sample from at least a first surface area of a substrate to the active collection surface area; and b) permit analysis of the sample concentrated on at least a first portion of the active collection surface area. In some embodiments, the sample may not be transferred from the at least first portion of the active collection surface area before being subjected to an analysis. In other embodiments, the sample may be transferred from the at least first portion of the active collection surface to another receptacle or material before analysis of the sample. In some embodiments, the device may be configured to detach the active collection component from the first portion of the handling component to permit analysis of the sample. In other embodiments, the device may be configured to detach the active collection component from both the first and the second portion of the handling component, which separates the active collection component entirely from the handling component. In yet other embodiments, the device may be configured to detach the active collection component from the second portion of the handling component. In various embodiments, the active collection component may include material configured to be compatible with reaction conditions of the analysis. In various embodiments, the active collection component may be configured in a sheet form. In some embodiments, the active collection component may include fibrous material. The fibrous material of the active collection component may include natural fibers, synthetic polymeric fibers or a combination thereof. In some embodiments, the fibrous material may be Nylon® fibers, cotton, Dacron, or paper, and optionally, where the fibrous material is chemically treated. In some embodiments, the fibrous material may be selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof.

In various embodiments of the sample collection device, the collecting of the sample to the at least first portion of the active collection surface area may concentrate the sample from the substrate. In some embodiments, the active collection surface area may be configured to be the surface area encompassing an exterior edge of an angled fold of the active collection component, where the angled fold is formed over a first portion of the handling component. In some embodiments, a length of the active collection component along the angled fold may be about 20 mm or less. In other embodiments, a length of the active collection component along the angled fold may be about 5 mm or less. In some embodiments, the exterior edge of the angled fold may form an acute angle. In other embodiments, the exterior edge of the angled fold may include a rolled edge having a diameter of less than about 3 mm. In various embodiments, the active collection surface area may be at least about 50% smaller than the at least first surface area of the substrate. In other embodiments, the active collection surface area may be at least about 90% smaller than the at least first surface area of the substrate.

In some embodiments of the sample collection device, the active collection component may be attached to the handling component via a pre-scored junction segment, where the pre-scored junction segment may be fractured to detach the active collection component from the second portion of the handling component. In some embodiments, the active collection component may be attached to the handling component via friction, vacuum or static charge. In other embodiments, the active collection component may be attached to the handling component with an adhesive. In yet other embodiments, the active collection component may be attached to the handling component via securing elements on the handling component. In some embodiments, the securing elements may be selected from O-rings, clips, snaps, pressurized fittings, or removable adhesive. In some embodiments, the active collection component has a disk shaped collection area.

In various embodiments of the sample collection device, the at least first portion of the active collection surface area may be one or more punches taken from the surface area encompassing the angled fold. The at least first portion of the active collection surface area may be configured to fit within a reaction volume of about 2 ul to about 100 ul. In other embodiments, the at least first portion of the active collection surface area may be configured to fit within a reaction volume of about 2 ul to about 50 ul. In other embodiments, the active collection surface area may also be configured to provide at least a second portion of the active collection surface area for archiving.

In various embodiments of the sample collection device, the active collection component may be connected to the first portion of the handling component by a detachable connector component. In some embodiments, the active collection component may be connected to the first portion of the handling component by at least a second surface area of the active collection component. In other embodiments, the active collection component may be attached to the first or the second portion of the handling component via clips or other pressurized fittings on the handling component which may be removed or released after sample collection. In other embodiments, the active collection component may be connected to the first portion of the handling component by at least a second surface area of the active collection component.

In various embodiments, the first portion of the handling component includes one or more layers of absorbent material underlying the active collection component. In various embodiments, the second portion of the handling component may be detachably connected to the active collection component. In various embodiments, the first portion of the handling component includes a stiffening support for the active collection component.

In some embodiments of the sample collection device, the sample collected to the active collection component may be a biological sample, an environmental sample, or an explosives residue sample. The sample may be a forensics sample. In some embodiments, when the sample includes nucleic acid then the analysis may be genetic analysis. In various embodiments, when the sample includes nucleic acid of an individual then the analysis may identify the individual. In other embodiments, when the sample includes nucleic acid of an animal, plant, bacteria or virus then the analysis may identify the animal, plant, bacteria or virus. In some other embodiments, when the sample is a biological sample or an environmental sample, potentially including at least one pathogen, then the analysis of the pathogen may be genetic analysis, microbiological analysis, protein analysis, or glycan analysis.

In various embodiments of the sample collection device, the active collection component, the handling component, or both may include an identifier to associate the sample with the substrate from which the sample was collected, where the identifier is alphanumeric, graphical, magnetic, or electromagnetic. In some embodiments, the identifier is a barcode. In various embodiments, the active collection component may include the identifier. In other embodiments, the at least first portion of the active collection component may include the identifier.

In yet another aspect, the invention provides a handling component including a support portion and a handle portion, where the handling component is configured to support an active collection component for collection of a sample. In some embodiments, the support portion of the handling component tapers to a thin edge. The support portion may taper to a thin edge having a width less than about 20 mm wide and having a thickness less than about 5 mm. In other embodiments, the support portion may taper to a thin edge having a width less than about 5 mm wide and a thickness of less than about 3 mm thick. The handle portion may be less than about 20 mm long. In some embodiments, the handling component is plastic.

In another aspect, the invention provides a kit including a sample collection device which includes an active collection component having a first surface area configured to be an active collection surface area; a handling component; where the active collection component is detachably connected to at least one of a first or a second portion of the handling component; and where the device is configured to: a) collect a sample from at least a first surface area of a substrate to the active collection surface area; and b) permit analysis of the sample concentrated on at least a first portion of the active collection surface area, and optionally, instructions for its use.

In some embodiments of the kit, the sample collection device may be configured to detach the active collection component from the first portion of the handling component to permit analysis of the sample. In other embodiments, the device may be configured to detach the active collection component from both the first and the second portion of the handling component, which separates the active collection component entirely from the handling component. In yet other embodiments, the device may be configured to detach the active collection component from the second portion of the handling component. In various embodiments, the active collection component may include material configured to be compatible with reaction conditions of the analysis. In various embodiments, the active collection component may be configured in a sheet form. In some embodiments, the active collection component may include fibrous material. The fibrous material of the active collection component may include natural fibers, synthetic polymeric fibers or a combination thereof. In some embodiments, the fibrous material may be Nylon® fibers, cotton, Dacron, or paper, and optionally, where the fibrous material is chemically treated. In some embodiments, the fibrous material may be selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof.

In some embodiments of the kit, the active collection surface area of the sample collection device may be configured to be the surface area encompassing an exterior edge of an angled fold of the active collection component, where the angled fold is formed over the first portion of the handling component. In some embodiments, a length of the active collection component along the angled fold may be about 20 mm or less. In other embodiments, a length of the active collection component along the angled fold may be about 5 mm or less. In some embodiments, the exterior edge of the angled fold may form an acute angle. In other embodiments, the exterior edge of the angled fold may include a rolled edge having a diameter of less than about 3 mm. In various embodiments, the active collection surface area may be at least about 50% smaller than the at least first surface area of the substrate. In other embodiments, the active collection surface area may be at least about 90% smaller than the at least first surface area of the substrate.

In some embodiments of the kit, the active collection component of the sample collection device may be attached to the handling component via a pre-scored junction segment, where the pre-scored junction segment may be fractured to detach the active collection component from the second portion of the handling component. In some embodiments, the active collection component may be attached to the handling component via friction, vacuum or static charge. In some embodiments the active collection component may be attached to the handling component with securing elements on the handling component. In some embodiments, the securing elements may be selected from O-rings, clips, snaps, pressurized fittings, or removable adhesive. In some embodiments, the active collection component has a disk shaped collection area. In some embodiments of the kit, the at least first portion of the active collection surface area of the sample collection device may be configured to fit within a reaction volume of about 2 ul to about 100 ul. In other embodiments, the at least first portion of the active collection surface area may be configured to fit within a reaction volume of about 2 ul to about 50 ul. In other embodiments, the active collection surface area may also be configured to provide at least a second portion of the active collection surface area for archiving.

In various embodiments of the kit, the active collection component of the sample collection device may be connected to the first portion of the handling component by a detachable connector component. In some embodiments, the active collection component may be connected to the first portion of the handling component by at least a second surface area of the active collection component. In other embodiments, the active collection component may be attached to the first or the second portion of the handling component via securing elements on the handling component which may be removed or released after sample collection. In some embodiments, the securing elements may be selected from O-rings, clips, snaps, pressurized fittings, or removable adhesive. In other embodiments, the active collection component may be connected to the first portion of the handling component by at least a second surface area of the active collection component.

In various embodiments, the first portion of the handling component includes one or more layers of absorbent material underlying the active collection component. In various embodiments, the second portion of the handling component may be detachably connected to the active collection component. In various embodiments, the first portion of the handling component includes a stiffening support for the active collection component.

In some embodiments, the kit may include one or more collection assistance liquids. In some embodiments, the collection assistance liquid is water, ethanol, or acetonitrile. In other embodiments, the kit may include reagents for stabilizing the sample on the active collection component of the sample collection device for archiving or shipping. In other embodiments, the kit further may include reagents for analysis of the sample. In other embodiments, the kit may further include at least one enclosure to protect the active collection component, the handling component, or both from contamination prior to use. In yet other embodiments, the kit may include at least one enclosure to protect the active collection component from contamination while archiving or shipping. In various embodiments of the kit, any combination of the active collection component, the handling component or the at least one enclosure may include an identifier to associate the sample with the substrate from which the sample was collected, where the identifier is alphanumeric, graphical, magnetic, or electromagnetic. In some embodiments, the identifier is a barcode.

In a further aspect, the invention provides a kit including a handling component including a support portion and a handle portion, where the handling component is configured to support an active collection component for collection of a sample, and optionally, instructions for use. In some embodiments, the support portion of the handling component tapers to a thin edge. The support portion may taper to a thin edge having a width less than about 20 mm wide and having a thickness less than about 5 mm. In other embodiments, the support portion may taper to a thin edge having a width less than about 5 mm wide and a thickness of less than about 3 mm thick. The handle portion may be less than about 20 mm long. In some embodiments, the handling component is plastic. In some embodiments, the kit further includes one or more active collection components. The active collection component may include an active collection surface area. In some embodiments, the active collection component is a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. The material for the active collection component may have a strip shape and may be of uniform width along its length. Alternatively, the material may be fabricated with a uniform width throughout its length, except at the active collection surface area supported by the tapered edge of the support portion of the handling component, where it may have a decreased width relative to the remainder of the active collection component. The kit may further include securing elements to attach the active collection component to the handling component, selected from the group of O-rings, snaps, clips, guideholes and securing pins, and double sided tape.

In another aspect, the invention provides a method for collection of a sample, including the steps of: providing a sample collection device which includes an active collection component having a first surface area configured to be an active collection surface area; a handling component; where the active collection component is detachably connected to at least one of a first or a second portion of the handling component; and where the device is configured to: a) collect a sample from at least a first surface area of a substrate to the active collection surface area; and b) permit analysis of the sample concentrated on at least a first portion of the active collection surface area; providing a substrate including a sample; and collecting the sample by contacting an active collection surface area of an active collection component of the sample collection device to at least a first surface area of the substrate. In some embodiments, the step of collecting the sample thereby concentrates the sample to the active collection surface area.

In some embodiments of the method for collection of a sample, the method may further include the step of detaching the active collection component from at least one of a first or a second portion of the handling component of the sample collection device. The method may further include the step of separating at least a first portion of the active collection surface area from the active collection component.

The method for collection of a sample may further include the step of providing an identifier to associate the sample collected to the active collection surface area with the substrate from which the sample was collected, where the identifier is alphanumeric, graphical, magnetic, or electromagnetic. The identifier may be a barcode.

In various embodiments of the method for collection of a sample, the method may further include the step of shipping the sample collection device including the sample to another location for archiving or testing. In other embodiments, the method may further include the step of shipping the active collection component including the sample to another location for archiving or testing.

In some embodiments of the method for collection of a sample, the sample may be a biological sample, an environmental sample, or an explosives residue sample. In some embodiments of the method, the sample may be a forensics sample.

In a further aspect, the invention provides a method of identification of a substance of interest which may be present in a sample on a substrate, including the steps of: providing a sample collection device which includes an active collection component having a first surface area configured to be an active collection surface area; a handling component; where the active collection component is detachably connected to at least one of a first or a second portion of the handling component; and where the device is configured to: a) collect the sample from at least a first surface area of a substrate to the active collection surface area; and b) permit analysis of the sample concentrated on at least a first portion of the active collection surface area; providing a substrate comprising a sample; and collecting the sample by contacting an active collection surface area of an active collection component of the sample collection device to at least a first surface area of the substrate; and subjecting the sample to an analysis to identify the substance of interest. In various embodiments, the analysis may be at least one of a polymerase chain reaction, a DNA sequencing reaction, STR analysis, SNP analysis, or Indel analysis. In various embodiments, the analysis may provide identification of a human.

In some embodiments of the method for identification of the substance of interest, the method may further include the step of detaching the active collection component from at least one of the first or the second portion of the handling component of the sample collection device. The method may further include the step of separating at least a first portion of the active collection surface area from the active collection component. The method may further include the step of providing an identifier to associate the sample collected to the active collection surface area with the substrate from which the sample was collected, where the identifier is alphanumeric, graphical, magnetic, or electromagnetic. The identifier may be a barcode.

In various embodiments of the method for identification of the substance of interest, the method may further include the step of shipping the sample collection device including the sample to another location for archiving or testing. In other embodiments, the method may further include the step of shipping the active collection component including the sample to another location for archiving or testing.

In various embodiments of the method for identification of the substance of interest, the method may further include the step of sending the identity of the substance of interest to at least one of a law enforcement agency, immigration control agency, forensics investigative agency, food safety agency, public health agency, or financial services agency.

In yet another aspect, the invention provides a process for manufacturing an edge swab, including the steps of fabricating a handling component including a support portion and a handle portion; fabricating an active collection component including an active collection surface area in a strip; placing the active collection surface area of the active collection component over the support portion to create an angled edge; and securing the active collection component to at least one of the support portion or the handle portion of the handling component. In some embodiments, the handling component is plastic. In some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the active collection component may be fabricated to have a uniform width. In other embodiments, the active collection component may be fabricated where the active collection surface area has a smaller width than the rest of the active collection component.

In another aspect, the invention provides a process for manufacturing a handling component including the steps of fabricating a support portion and a handle portion. In some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the handling component is plastic.

In the following description, certain aspects and embodiments will become evident. It should be understood that a given embodiment need not have all aspects and features described herein. It should be understood that these aspects and embodiments are merely exemplary and explanatory and are not restrictive of the invention.

There still exists a need for improved devices, kits, and methods for collecting fingerprint and biological sample data for purposes of identifying and confirming the identity of a human individual.

BRIEF DESCRIPTION OF THE DRAWINGS

The skilled artisan will understand that the drawings described below are for illustration purposes only. The drawings are not intended to limit the scope of the present teachings in any way.

FIG. 1A is a graphical representation of an edge swab, which is one example of a sample collection device, and how to assemble it.

FIG. 2A is a graphical representation of another embodiment of an edge swab and an enlargement showing the active collection surface area.

FIG. 2B is a graphical representation of two other embodiments of edge swabs.

FIG. 2D is a graphical representation of another embodiment of an edge swab and a graphical representation of a rolled edge of the active collection surface area of another embodiment of an edge swab.

DETAILED DESCRIPTION

Figure 1B:
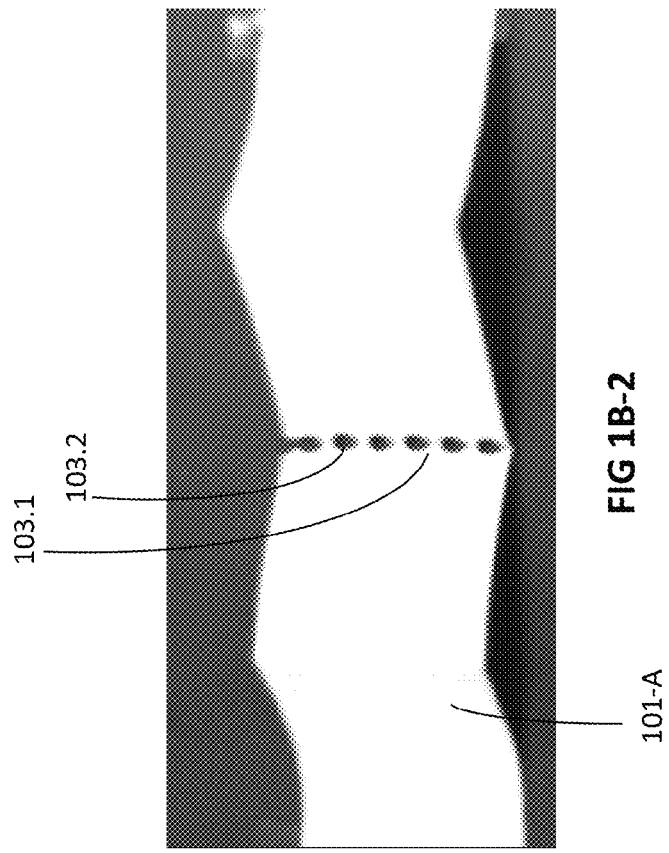
FIG. 1B is a graphical representation of the operation of the edge swab and an example of the active collection component after portions of the active collection surface areas have been removed for archiving or analysis.

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used here, "DNA" and "nucleic acid" are used interchangeably.

As used here, "oligonucleotide" and "polynucleotide" are interchangeable and generally refers to a polymer of nucleotide subunits having a fragment size of about or less than 200 base pairs.

As used here, "biological sample" refers to a component originating from either within or on the surface of a human animal, a non-human animal, a plant, a fungus, a bacteria, or a virus.

As used here, "DNA sequencing" refers to the determination of the sequential identity of nucleotides in a molecule of DNA.

As used here, "filter paper" refers to a semi-permeable paper.

As used here, "identifier" refers to a label capable of use in cataloging/correlating like-labeled data or data from a single source.

As used here, "Indel" refers to an insertion or deletion of a segment of nucleic acid, usually DNA, within a nucleic acid sequence.

As used here, "Individual" refers to a human.

As used here, "Genetic markers" or more simply, "markers" are generally alleles of genomic DNA loci with characteristics of interest for analysis, such as DNA typing, in which individuals are differentiated based on variations in their DNA. Most DNA typing methods are designed to detect and analyze differences in the length and/or sequence of one or more regions of DNA markers known to appear in at least two different forms, or alleles, in a population. Such variation is referred to as "polymorphism," and any region of DNA in which such a variation occurs is referred to as a "polymorphic locus." One possible method of performing DNA typing involves the joining of PCR amplification technology (K B Mullis, U.S. Pat. No. 4,683,202) with the analysis of length variation polymorphisms. PCR traditionally could only be used to amplify relatively small DNA segments reliably; i.e., only amplifying DNA segments under 3,000 bases in length (M. Ponce and L. Micol (1992), NAR 20(3):623; R. Decorte et al. (1990), DNA CELL BIOL. 9(6):461 469). Short tandem repeats (STRs), minisatellites and variable number of tandem repeats (VNTRs) are some examples of length variation polymorphisms. DNA segments containing minisatellites or VNTRs are generally too long to be amplified reliably by PCR. By contrast STRs, containing repeat units of approximately three to seven nucleotides, are short enough to be useful as genetic markers in PCR applications, because amplification protocols can be designed to produce smaller products than are possible from the other variable length regions of DNA.

As used here, "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

As used here, the term "sample containing nucleic acid" refers to nucleic acid found in biological samples according to the present invention including, but not limited to, for example, hair, feces, blood, tissue, urine, saliva, cheek cells, vaginal cells, skin, for example skin cells contained in fingerprints, bone, tooth, buccal sample, amniotic fluid containing placental cells, and amniotic fluid containing fetal cells and semen. It is contemplated that samples may be collected invasively or noninvasively. The sample can be on, in, within, from or found in conjunction with a fiber, fabric, cigarette, chewing gum, adhesive material, soil or inanimate objects.

As used here, "SNP analysis" refers to the evaluation of the presence or absence of a single nucleotide polymorphism (SNP) marker following amplification of the locus containing the SNP marker.

As used here, "STR analysis" refers to the evaluation of the alleles of a short tandem repeat (STR) marker following amplification of the locus containing the STR marker.

As used here, "substrate suitable for electrophoresis" refers to a matrix which can support the migration of species, including but not limited to nucleic acids when exposed to an electrical current such as electrophoresis.

Reference will now be made to various embodiments, examples of which are illustrated in the accompanying drawings. The present invention relates to devices, kits, and methods for collecting a sample from a substrate. The devices, kits, and methods also permit analysis to be made more efficiently of a substance of interest potentially present in the collected sample. The devices, kits and methods according to the invention can find use in a wide variety of applications, including but not limited to, identification of individuals, identification of animals, plants, and other organisms, forensics, food safety, importation controls, identification of chemical, biosynthetic or bioproduction intermediate, metabolite or products, environmental analyses, medical outbreak response, explosives analysis, and the like. The results arising from the analysis may be of use to organizations responsible for criminal investigation, human identity, child identity, missing persons, immigration, terrorist, paternity, arrestee, access control, importation control, food safety, insurance investigation, health organizations, vector control, emergency response or penal control.

Improvements are needed for collection of samples. The act of collecting a sample that may contain a substance of interest does not typically provide identification of whether the substance is present and in various scenarios, the amount of sample available for collection may be very limited. Currently available sampling devices include swabs or sticky tapes that require chemical extraction before the substance of interest may be analyzed and identified. Additionally, physical concentration of the extracted sample is often an additional required step, as the current sampling devices have large undefined surface areas where sample has been collected.

There is therefore a need for sample collection devices configured to collect even small quantities of a sample and configured to facilitate analysis of a potential substance of interest within the sample, Improved sample collection devices and their use are described here which are configured to collect a sample that may contain a substance of interest and facilitate analysis of even a very small quantity of the substance capable of being detected by the analysis. In various embodiments, no additional transfer of the sample is required before subjecting the sample to analysis for the substance of interest. In some embodiments, devices, systems, and methods are disclosed to concentrate the sample by collection from a substrate to an active collection component for further processing such as lysis or for analysis identifying the substance of interest that may be present within the sample.

Sample Collection Device. A sample collection device, according to various aspects of the invention, includes an active collection component having a first surface area forming an active collection surface area and a handling component, where the active collection component is detachably connected to at least one of a first or second portion of the handling component; and where the device is configured to: a) collect a sample from at least a first surface area of a substrate to the active collection surface area; and b) permit analysis of the sample concentrated on at least a first portion of the active collection surface area. In various embodiments, the sample may be not transferred from the at least first portion of the active collection surface area before being subjected to an analysis. In other embodiments, when the sample is collected to the at least first portion of the active collection surface, then the sample may be concentrated relative to its distribution on the substrate.

Active Collection Component. The sample collection device may be configured to detach the active collection component from at least one of a first or a second portion of the handling component to permit analysis of the sample. The active collection component may be attached to the first or the second portion of the handling component via adhesive that may be disrupted after sample collection. The active collection component may be attached to the handling component via securing elements on the second portion of the handling component which may be removed or released after sample collection. The securing elements may include, but are not limited to, clips, snaps, O-rings, other pressurized fittings, or adhesive that is removable. The active collection component may be detachable from the handling component by tearing one or more perforated junctions between the active collection component and the second portion of the handling component. In other embodiments, the active collection component may be connected to the first portion of the handling component by at least a second surface area of the active collection component. In some embodiments, the at least second surface area of the active collection component is a surface area on the opposite face of the active collection component from the active surface area.

In some embodiments, the active collection component is attached to the handling component via a pre-scored junction segment, wherein the pre-scored junction segment may be fractured to detach the active collection component from the second portion of the handling component. In some embodiments, when the active collection component is detached by fracturing the pre-scored junction segment, the first portion of the handling component remains with the active collection component. In other embodiments, the active collection component is attached to the handling component via friction, vacuum or static charge.

The active collection component may be shaped in a variety of configurations. One nonlimiting shape includes a strip shape. The active collection component may have different widths at various points along the strip shape, in order to provide either larger or smaller dimensions to the active collection surface area. In other embodiments, the active collection component may be formed in a disk, curved, or cupped shape. The active collection component may have a disk shaped active collection surface area. In other embodiments, the active collection surface area and the active collection component surrounding it may be configured in a complex shape, in order to facilitate collecting a sample from a hard to reach location such as the inside surface of a car door handle.

The active collection component may be formed of a material configured to be compatible with reaction conditions of an analysis performed on the sample. The active collection component may be configured in a sheet form.

The active collection component may be formed from any suitable fibrous material. Suitable fibrous material includes natural fibers, synthetic polymeric fibers or a combination thereof.

The active collection component can be a paper material selected from Whatman® paper, including W-903 paper, FTA™ paper, FTA™ Elute paper, FTA™ 1 DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof.

In some embodiments, the active collection component may be an anion exchange membrane. (e.g., AMI-7001, available from Membranes International Inc., Ringwood, N.J.) In one non-limiting example, the anion exchange membrane may be made of polystyrene/divinyl benzene co-polymers that have been functionalized with quaternary amine groups. The functionalized membrane may attract substances of interest contained in the sample, including but not limited to nucleic acids. In other embodiments, an ion exchange membrane (Pall Corporation, Ann Arbor, Mich.) can be used for capturing a sample from a substrate.

In some embodiments, the active collection component may be formed of a material suitable as a matrix for mass spectrometry, atomic analysis, or microbiological analysis. In other embodiments, the active collection component may be formed of a material compatible with PCR, protein analysis, antibody labeling, and dye labeling or glycan analysis.

In various embodiments, the active collection component may comprise a polymeric film to collect the sample from the substrate. Useful polymeric films include natural polymeric materials, which include but are not limited to starch, agarose, alginate, carrageenan or synthetic polymer gel, or a mixture thereof.

Synthetic polymers may also be used as the active collection component. To form the polymeric film or fiber that may be used as an active collection component, all types of polymerization, including cationic, anionic, copolymerization, chain copolymerization, cross-linking, uncrosslinked polymerization, and the like can be employed to synthesize the polymer gels forming part or all of the active collection component. Essentially any type of polymer or copolymer formable from a fluid precursor, including but not limited to homopolymers, random copolymers, terblock polymers, radial polymers, linear polymers, branched polymers, and graft copolymers, can be incorporated onto the support as part of all of the substrate. An exemplary, non-limiting list of polymers that are suitable include cellulose polymers, including but not limited to hydroxyethylcellulose (HEC), hydroxypropyl methylcellulose (HPMC), hydroxypropyl cellulose (HPC); derivatives of sugars including but not limited to dextrans, mannitols, and gluco-pyranosides; pluronic copolymer liquid crystals; polyurethane; polyacids, including but not limited to lactic acids, and acrylic acids; polyamides; polyacrylamides, including but not limited to unsubstituted, N-substituted, and N, N-disubstituted acrylamides; polycarbonates; polyacetylenes; polydiacetylenes; polyphosphazenes; polysiloxane; polyolefins; polyesters; polyethers; poly(ether ketones); poly(alkylene oxides), including but not limited to polyethyleneoxides (PEO), polyethylethylene glycols (PEG) and polypropylene oxides (PPO); poly(ethylene terephthalate); poly(methyl methacrylate); polystyrene; substituted polystyrene, including but not limited to polystyrene sulfonates (PSS) and polyanetholes (PASA); poly(vinylpyrrolidones); proteinaceous material, and/or combinations and/or copolymers of the above.

In some embodiments, the active collection component may be modified with chemically reactive groups to permit ionic, covalent or hydrogen bond interactions with species present within the biological sample. Suitable chemically reactive groups that may modify an active collection component include but are not limited to thiols, amines, carboxylic acids or the like, as is generally known in the art. Some examples of chemical modifications include, but are not limited to, amino groups including aliphatic and aromatic amines, carboxylic acids, aldehydes, amides, chloromethyl groups, hydrazide, hydroxyl groups, sulfonates and phosphates. These functional groups can be used to add any number of modifications to the polymeric active collection component, generally using known chemistries, including, but not limited to the use of amino-functionalized linkers, sulfhydryl linkers, etc. There are a number of sulfhydryl reactive linkers known in the art such as SPDP, maleimides, alpha-haloacetyls, and pyridyl disulfides. Similarly, amino groups may be attached to the active collection component using linkers; for example, a large number of stable bifunctional groups are well known in the art, including homobifunctional and heterobifunctional linkers. In an additional embodiment, carboxyl groups on the active collection component can be derivatized using well-known linkers. For example, carbodiimides activate carboxyl groups for attack by good nucleophiles such as amines.

In some embodiments, the chemical modification of the active collection component is performed to attach, covalently or noncovalently, a reagent, including but not limited to an enzyme, a binding partner, a surfactant, an anionic polymer or a zwitterionic species to assist in the collection of the sample from the substrate. In some embodiments, the chemical modification may introduce electrically conductive polymers to the active collection component, to assist in collection of the sample from the substrate, for example, DNA. If conductive polymers form part of the active collection component, the system may further provide suitable electrical flow across the active collection component to provide ionotophoretic assistance to drive charged nucleic acids from the substrate to the active collection component, when the electrical circuit is completed.

In yet other embodiments, when an active collection component is modified chemically to covalently attach one or more reagents, an enzyme, including but not limited to proteinase K may be attached to the active collection component to assist in extracting one or more substances of interest from the sample once collected. In other embodiments, an enzyme is covalently attached to the active collection component, and may be a proteinase selected from the group consisting of keratinase, papain, bromelain, and proteinase K. In other embodiments, the active collection component is modified covalently to attach a charged polymer to assist in extracting a substance of interest, including but not limited to nucleic acids, from the sample once collected. In yet other embodiments, a surfactant is associated with the active collection component noncovalently to assist in extracting a substance of interest, including but not limited to nucleic acids, from the sample once collected. In some embodiments, a zwitterionic species may be present in the active collection component to assist in separating a substance of interest, including but not limited to nucleic acids, from other components of the sample. In some other embodiments, the active collection component is chemically modified to covalently attach an antibody to a target moiety potentially present in the sample, thus providing a binding partner to the target moiety. In some embodiments, where a binding partner is immobilized on the active collection component, cleavage of the binding partner along with or separately from its binding target moiety may be performed.

In some embodiments, the polymeric active collection component is modified to be adhesive. In other embodiments, the polymeric active collection component is tackified, assisting in collection of the biological sample, without leading to physical handling difficulties.

In some embodiments, the polymeric active collection component has no modifications made to the film or fiber from which the polymeric active collection component is made.

Some embodiments of the active collection component permit transfer of the sample, once collected to the active collection component, to another receptacle or material for analysis of the sample. In some embodiments, the active collection component permits transfer of the sample via rinsing. In other embodiments, the active collection component permits transfer of the sample via alteration of its characteristics, such as electric charge, or release from a chemically modified film or fiber. Other suitable active collection components permit direct analysis of the sample, collected from the substrate, in the presence of the active collection component.

Active Collection Surface Area. The active collection surface area is configured to collect a sample from at least a first surface area of a substrate. The active collection surface area of the active collection component may be configured in a variety of configurations, and a person of skill can determine that the following descriptions are not meant to limit the number of possible configurations. The active collection surface area may have an oblong configuration, circular, or cupped shape.

In one embodiment, the active collection surface area is configured to be the surface area encompassing an exterior edge of an angled fold of the active collection component, where the angled fold is formed over a first portion of the handling component. In some embodiments, a length of the active collection component along the angled fold may be about 20 mm or less. The length of the active collection component along the angled fold may be about 10 mm or less. In other embodiments, the length of the active collection component along the angled fold may be about 5 mm or less. In some embodiments, the angled fold of the active collection component may form an acute angle, i.e., less than 90 degrees. In various embodiments of the active collection surface area encompassing an exterior edge of an angled fold of the active collection component, the width of the active surface area from the angled fold may be about 5 mm or less. In other embodiments, the width of the active collection surface area from the angled fold may be about 3 mm or less. In yet other embodiments the width of the active collection surface area from the angled fold may be about 2 mm or less. Non-limiting examples of various active collection surface areas having an exterior edge of an angled fold of the active collection component are shown in FIGS. 1-3. In various embodiments, the exterior edge of the angled fold includes an angled fold that may be a rolled edge having a diameter of less than about 5 mm. In some embodiments, the exterior edge of the angled fold includes an angled fold that may include a rolled edge having a diameter of less than about 3 mm. One example of a rolled angled edge is shown in FIG. 2D-6, where the exterior rolled angled fold is formed around a dowel shaped support having a diameter of 5 mm or less. In various embodiments, the active collection surface area may be formed along an edge that is curved or circular.

In various embodiments, the active collection surface area is smaller than the at least first surface area of a substrate from which a sample is collected, and concentrates a potentially limited amount of sample to the active collection surface area. In some embodiments, the active collection surface area is at least about 50% smaller than the at least first surface area of the substrate. In other embodiments, the active collection surface area is at least about 90% smaller than the at least first surface area of the substrate. In yet other embodiments, the active collection surface area is at least about 200% smaller than the at least first surface area of the substrate. In some embodiments, the active collection surface area is configured to be small enough to permit swabbing of a large substrate area to collect a sample containing a substance of interest that may be present in a concentration at or below the detectable limit of the substance as originally present on the substrate.

The active collection surface area is configured to permit analysis of the sample concentrated on at least a first portion of the active collection surface area. In some embodiments, the entire active collection surface area, containing at least some of the collected sample, is submitted to analysis. In some embodiments, the at least first portion of the active collection surface area may be one or more punches taken from the surface area encompassing the angled fold. The punches may be of any shape. In some embodiments, the at least first portion of the active collection surface area is configured to fit within a reaction volume of about 2 ul to about 100 ul. In other embodiments, the at least first portion of the active surface area is configured to fit within a reaction volume of about 2 ul to about 50 ul. In various embodiments, the active collection surface area is configured to provide at least a second portion of the active collection surface area for archiving.

Handling Component. The sample collection device is configured to include a handling component configured to support the active collection component and permit collection of the sample from the substrate. The handling component may include at least a first portion that supports the active collection component and may additionally include a second portion that provides a handle for ease of operation and, optionally, for providing force when contacting the substrate. In some embodiments, the handling component is configured to detach the active collection component from at least one of the first or the second portion of the handling component to permit analysis of the sample. The active collection component may be attached to the handling component via adhesive that may be disrupted after sample collection. The active collection component may be attached to the handling component via securing elements such as clips, snaps, O-rings, guideholes and pins, guiding loops or other pressurized fittings on either the first portion or the second portion of the handling component which may be removed or released after sample collection. In some embodiments, the securing elements may not attach the active collection component but may offer improved grip for the operator. In other embodiments, the active collection component may be connected to the first portion of the handling component by at least a second surface area of the active collection component. In some embodiments, the at least second surface area of the active collection component is a surface area on the opposite face of the active collection component from the active surface area.

In various embodiments, the active collection component is connected to the first portion of the handling component by a detachable connector component. In some embodiments, the active collection component is attached to the handling component via a pre-scored junction segment, wherein the pre-scored junction segment may be fractured to detach the active collection component from the second portion of the handling component. In other embodiments, the active collection component is attached to the first portion of the handling component via friction, vacuum or static charge.

In some embodiments, the first support portion of the handling component may be a stiffening support for the active collection component. The stiffening support for the active collection component may taper to a thin edge, to support and create the angled fold of the active collection component. The tapered edge of the stiffening support of the handling component may have thickness of about 5 mm or less. In other embodiments, the tapered edge of the stiffening support may have a thickness of about 3 mm or less. In some other embodiments, the tapered edge of the stiffening support of the handling component may have a thickness of about 0.9 mm or less. The tapered edge of the stiffening support may have a width of about 20 mm or less. In some embodiments, the tapered edge of the stiffening support may have a width of about 5 mm or less. In other embodiments, the second portion of the handling component may be a stiffening handle portion for ease of collecting the sample from the substrate. The length of the handle portion may be about 20 mm in some embodiments or may be selected to be of any convenient length for contacting the substrate with ease of operation. The stiffening handle portion may be the same material for both the first and the second portions of the handling component.

In another embodiment the stiffening support of the first portion of the handling component may be configured as a convex base, where the active collection component is formed over the convex base forming a convex shape that contacts the substrate.

The stiffening support of the handling component may be made of any material capable of forming a solid base. A suitable material for a support may have any of a variety of properties depending upon the particular embodiments, including for example, porous, nonporous, rigid, elastic, pliable, malleable, low temperature melting, high temperature melting, and/or chemically resistant to one or more solvents commonly used in the reactions set forth herein. In some embodiments, the support is formed from a material selected from a stiffened paper, a wood product, a polymer, a metal, a metal alloy, a glass, a silicon material or combinations thereof. Suitable polymers include but are not limited to, plastic; polypropylene, polyethylene, polybutylene, polyurethane, nylon, polymer such as acrylic, acrylonitrile butadiene styrene (ABS), ULTEM (Polyetherimide), acetal copolymer, PROPYLUX HS (heat stabilized polypropylene), RADEL A (polyethersulfone), RADEL R (polyarylethersulfone), UDEL (polysulfone), NORYL PPO (polyphenylene oxide & styrene), Polycarbonate, UHMW-PE (ultra high molecular weight polyethylene), Polyetheretherketone (PEEK), polyphenylene sulfide (PPS, TECHTRON or RYTON), polyolefin or polystyrene; metal such as aluminum, iron, steel or an alloy; other materials such as glass or silicon, or derivatives or combinations of these or other suitable materials.

The stiffening support of the handling component may be formed to underlay the entire active collection component, or underlay part of the active collection component.

Handling Component Including Further Absorptive/Transport Features. In various embodiments, the first portion of the handling component includes one or more absorptive layers underlying the active collection component, and in particular, the active collection surface area. The one or more absorptive layers of the handling component underlying the active collection component may be configured to be detached from the active collection component after the sample is collected, and before the portion(s) of the active collection surface area are removed for analysis. The one or more absorptive layers of the handling component may include paper, polymer or desiccant materials. The one or more absorptive layers of the handling component may be thicker than that of the active collection component, thereby absorbing more fluid, and leaving larger biomolecules collected to the active collection surface area. An active collection surface area having a thinner layer may permit a greater number of punches selected from it to increase the amount of sample while still fitting within a reaction volume of the analysis.

In other embodiments, additional wicking behavior may be obtained by creating an active collection component having relatively thinner layer at the active collection surface area, and relatively thicker layer surrounding the active collection surface area. This may provide relatively higher concentration of a higher molecular weight species such as nucleic acid at the active collection surface area, and decreased amounts of smaller molecular weight species, which may be of lesser interest in this particular example.

The handling component may also include other transport features, including but not limited to a user operated vacuum source embedded within the handling component and underlying the active collection component. This may permit active aspiration of fluid from the active collection surface area and provide concentration of the sample on the active collection surface area. The handling component may also include an aerosol functionality that may deliver a precisely metered amount of a collection assistance liquid, such as water, ethanol or acetonitrile as the sample collection device collects the sample from the substrate. The handling component may also include an aerosol functionality that may deliver a precisely metered amount of a collection assistance liquid, such as water, ethanol or acetonitrile as the sample concentration device collects the biological sample from the substrate. The handle portion may be configured have a different range of lengths and may also be configured to include additional attachments for installation and use of an edge swab in an automated instrument, where the automated instrument performs the action of concentrating the biological sample from the substrate to the active collection surface area of the active collection component.

Process of Manufacturing an Edge Swab. Edge swabs, as described here, may include a handling component and an active collection component, and may be manufactured in a number of ways. The handling component may be manufactured of plastic or cardboard, amongst other materials. If the handling component is made of a plastic, it may be 3D printed or it may be injection molded. Alternatively, the handling component may be made of wood, metal, or cardboard and shaped by laser cutting.

In various embodiments, the handling component has a first portion configured to be a support portion and a second portion configured to be a handle portion. The first support portion of the handling component may provide stiffening support for the active collection component. The stiffening support portion may be fabricated to taper to a thin edge, to support and create the angled fold of the active collection component. The tapered edge of the stiffening support of the handling component may be fabricated to have a thickness of about 5 mm or less. In other embodiments, the tapered edge of the stiffening support may be fabricated to have a thickness of about 3 mm or less. In some other embodiments, the tapered edge of the stiffening support of the handling component may be fabricated to have a thickness of about 0.9 mm or less. The tapered edge of the stiffening support may have a width of about 20 mm or less. In some embodiments, the tapered edge of the stiffening support may be fabricated to have a width of about 5 mm or less. The handle portion may have a length of about 20 mm or less. In other embodiments, the handle portion may have a length of about 100 mm or less. The other dimensions of the support portion of the handling component may be selected as appropriate for the particular use of the edge swab, to support the remainder of the active collection component at regions away from the angled fold while permitting the edge swab to easily contact the substrate.

In various embodiments, the second portion of the handling component may be fabricated to be a stiffening support for a handle for ease of collecting the sample from the substrate. The handling component may be manufactured in many different configurations, as shown in FIGS. 1A-B, 2A-E and 3. The length of the handle portion may be about 20 mm in some embodiments. The length of the handle portion of the handling component may be longer, and in some embodiments, such as that shown in FIG. 2E, significantly longer than 20 mm, in order to collect a sample from a hard to reach substrate or surface. The handle portion may be configured have a different range of lengths and may also be configured to include additional attachments for installation and use of an edge swab in an automated instrument, where the automated instrument performs the action of concentrating the biological sample from the substrate to the active collection surface area of the active collection component.

The active collection component of the edge swab may be made of any suitable material as described above. It may be fabricated in a sheet form, and in some embodiments, the sheet is of uniform thickness. In other embodiments, it is fabricated with a variable thickness, and in particular, may be fabricated to be thin where it is supported by the tapered edge of the support portion of the handling component, which forms the angled fold of the edge swab, and thicker elsewhere to provide more wicking capability or strength as it is secured to at least one of the support or the handle portion. In some embodiments, the active collection component is fabricated from a paper such as a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. The material for the active collection component may be fabricated to be a strip shape and may be of uniform length and width. Alternatively, the material may be fabricated with a uniform width throughout its length, except at the region (active collection surface area) that is supported by the tapered edge of the support portion of the handling component, where it may have a decreased width relative to the remainder of the active collection component. In some embodiments, the strip may be about 5 mm by about 80 mm. Alternatively, the strip may be about 20 mm by about 100 mm. In some embodiments, the active collection surface area is about 1 mm by about 5 mm wide.

The active collection component may be fabricated to be secured by securing elements such as O-rings at one or more locations along the handle portion of the handling component. The active collection component may be secured by securing elements including but not limited to clips, snaps, clamps, or other fittings on the handle portion or the support portion of the handling component, where the securing element holds a portion of the strip of the collection component in tension against the handling component. Alternatively, the active collection component may be fabricated with double sided tape securing it to the handling component. In another embodiment, the handle portion of the handling component may be fabricated to have a guide hole piercing the handle, where each of both ends of the strip of the active collection component is fabricated with a through-hole at each end. The edge swab is assembled by placing the active collection component in place over the tapered edge of the support portion and aligning the through-holes of the active collection component with the pierced hole in the handle portion and securing all three sections with a rod or pin. In yet another embodiment, the handle portion of the handling component includes guide loops thru which each end of the active collection component passes and is secured. The securing elements may also provide ease of operation during the collection of the sample.

The edge swab may be preassembled before use, or it may be supplied to an end user unassembled. The handling component may be made available in a kit to the end user separately from the active collection component.

In yet another aspect, the invention provides a process for manufacturing an edge swab, including the steps of fabricating a handling component including a support portion and a handle portion; fabricating an active collection component including an active collection surface area in a strip; placing the active collection surface area of the active collection component over the support portion to create an angled edge; and securing the active collection component to at least one of the support portion or the handle portion of the handling component. In some embodiments, the handling component is plastic. In some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the active collection component may be fabricated to have a uniform width. In other embodiments, the active collection component may be fabricated where the active collection surface area has a smaller width than the rest of the active collection component.

In another aspect, the invention provides a process for manufacturing a handling component including the steps of fabricating a support portion and a handle portion. In some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the handling component is plastic.

Some non-limiting exemplary embodiments of the sample collection device are shown in the following paragraphs.

Figure 1B:
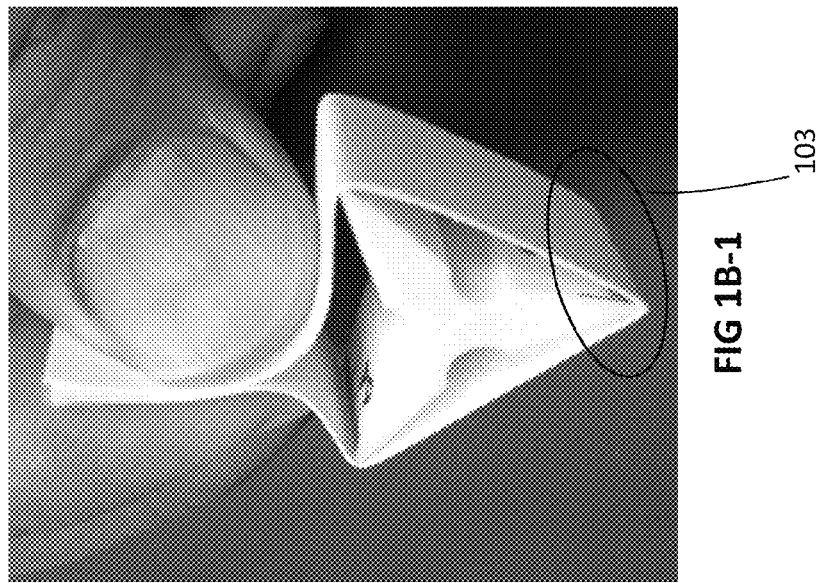

FIGS. 1A-B show various aspects of preparation and usage of an edge swab, which belongs to one class of the sample collection devices described here. In FIG. 1A-1, the separate components of an edge swab is shown, where the handling component is represented by support element 102, and the active collection component 101 is shown, where the material forming the active collection component is a sheet and configured as a strip. In FIG. 1A-2, the assembled edge swab is shown where element 103 represents the active collection surface area that contacts a substrate to collect a sample. The handling component support element 102 is detachably connected to the active collection component by friction, and the support element underlays and supports the active collection component to form an angled fold having an exterior angled edge 103. The outer surface 101-1 of the active collection component 101 has a portion of its surface area that is the active collection surface area, while the opposing side of the strip, 101-2 detachably connects with the support element 102. FIG. 1B-1 shows an operator controlling the edge swab capable of exerting pressure, if needed, upon a substrate to collect a sample along the active collection surface area 103 which encompasses the angled fold supported by handling component support element 102. After the sample is collected, FIG. 1B-2 shows the active collection component after detachment from the support element 102, and further shows that at least one portion, punch 103.1 has been selected from the active collection surface area 103 and removed for analysis, where another punch 103.2 may also be used in the analysis or archived, and where the remainder of the active collection component 101-A may also be retained for archiving.

FIG. 2A -1A shows another embodiment of an edge swab which is a sample collection device as described here. This edge swab device may have a handle portion 204-1 and active collection component 201 (with outer surface 201.1-1, and inner surface 201.2-1) attached to the handle portion 204-1. The active collection component may be easily detached from the handle portion through various kinds of simple mechanical mechanisms such as by incorporating a snap point near the end of the handle, for example securing elements 208.1-1 and 208.2-1. In some embodiments, the securing elements may not attach the active collection component but may offer improved grip for the operator. In some embodiments, the handle portion 204-1 is made of a single piece of rigid material extending to a support portion 202-1, of the handling component 209-1. The support portion 202-1 underlays the active collection surface area 203-1 of the active collection component, and creates an angled fold. The active collection surface area 203-1 is the surface area encompassing the angled edge supported by support portion 202-1, which can collect and concentrate the sample containing a substance of interest to the small surface area of 203-1, which in this embodiment has a length of about 20 mm. FIG. 2A-1 B shows an enlargement of the active collection component showing the outer surface 201.1-B of the active collection component material as it is configured around the angled shaft of the support portion 202-1B underlying the active collection surface area 203-1 B. In some embodiments the width of the active collection surface area is about 20 mm. The device of FIG. 2A-1B may be swabbed with or without some pressure to collect a sample from a substrate to concentrate the sample to active collection surface area 203-1B.

FIG. 2B shows two other embodiments of an edge swab according to various aspects of the invention.

In FIG. 2B-2, one embodiment of an edge swab having a narrow strip of active collection component is shown, the outer surface of which 201.1-2 is visible, which is attached to the handling component of the edge swab via clips, or other pressurized removable fittings at securing elements 208.1-2 and 208.2-2. The active collection surface area 203-2 encompasses the angled fold and is about 5 mm wide. It is supported by handling component support portion 202-2 which is connected to handle portion 204-2 of the handling component 209-2.

In FIG. 2B-3, another embodiment of an edge swab having a narrow strip of active collection component at the active collection surface area 203-3 encompassing the angled fold, and having a width of about 5 mm, but the active collection component broadens to form a wider active collection component (the outer surface 201.1-3 and the inner surface 201.2-3), which continues to a detachable connection at clip or friction fittings at securing elements 208.1-3 and 208.2-3 at the end of the handle portion 204-3 of the handling component 209-3, which has a support portion 202-3 which underlays the angled fold and active collection surface area. The connection of the active collection component 201.1-3 may also be effected by removable adhesive applied to the inner surface 201.2-3 at a point along the handle portion 204-3 or alternatively, the active collection component may be perforated where it meets securing elements 208.1-3 and 208.2-3.

Figure 2C:
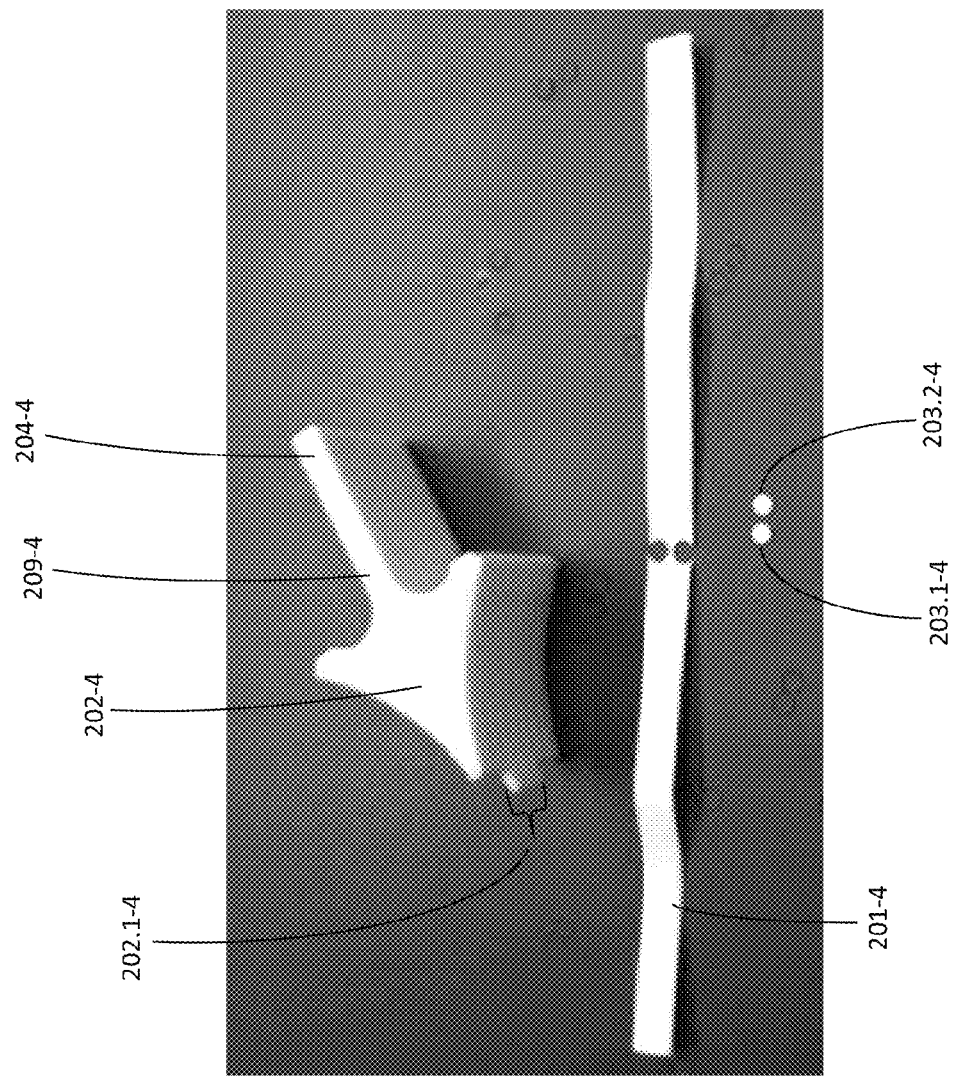
FIG. 2C is a graphical representation of another embodiment of an edge swab and its components after a sample has been collected.
Figure 3:
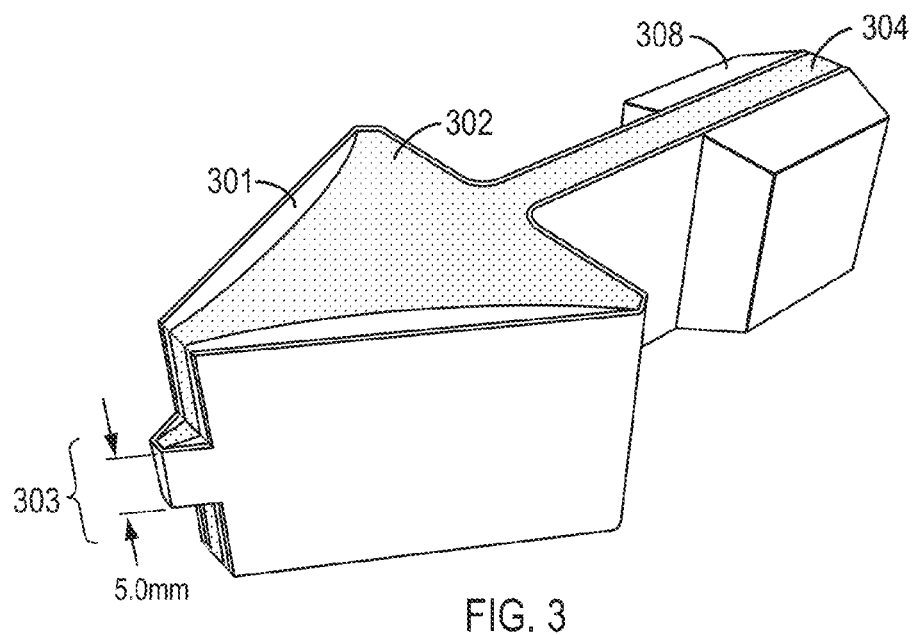
FIG. 3 is a graphical representation of another embodiment of an edge swab.

FIG. 2C shows another embodiment of an edge swab. The components of the edge swab are shown after a sample has been collected, the active collection component has been detached from the handling component and the portions of the active collection surface area have been selected out from the active collection component. The handling component 209-4 is composed of two portions, the support portion 202-4 and the handle portion 204-4. As is shown in the figure, this support portion has a protruding segment 202.1-4 of the support portion which provides the stiffening support for the active collection component 201-4. The active collection component 201-4 is shown after the sample has been collected, and the active collection component has been detached from both the support 202-4 and the handle 204-4 portions of the handling component 209-4. Portions 203.1-4 and 203.2-4 have been removed from the active collection component, in particular from the active collection surface area encompassing the angled fold formed by the protruding 202.1-4 portion of the support component 202-4. The portions 203.1-4 and 203.2-4 of the active collection surface area may be used for analysis or for archiving.

FIG. 2D-5 shows yet another embodiment of an edge swab. The handling component 209-5 is composed of a support portion 202-5 connected to a handle portion 204-5. For this support component, the tapered edge of the support component has a width across the taper of about 0.9 mm to underlay and support the angled fold of the active collection component (having an outer surface 201.1-5 that forms the exterior edge of the angled fold, and an inner surface 201.2-5). The active collection surface area 203-5 is the area encompassing the angled fold and is about 20 mm wide in this embodiment. The active collection component is detachably connected to the handling component either by friction created by securing elements 208.1-5 and 208.2-5 or with removable adhesive to any part of the handle portion 204-5 of the handling component 209-5.

FIG. 2D-6 is an edge-on view of a rolled edge swab, where the angled fold is a semi-circular region formed around a rounded support component, not shown in this view. The diameter of the rolled angle is about 4 mm in this embodiment, and provides an active collection surface area encompassing this region 203.A-6. The width of the active collection surface area is the dimension shown as 203.B-6. The 4 mm region of 203.A-6 can contact the substrate to collect sample along the width 203.B-6.

Figure 2E:
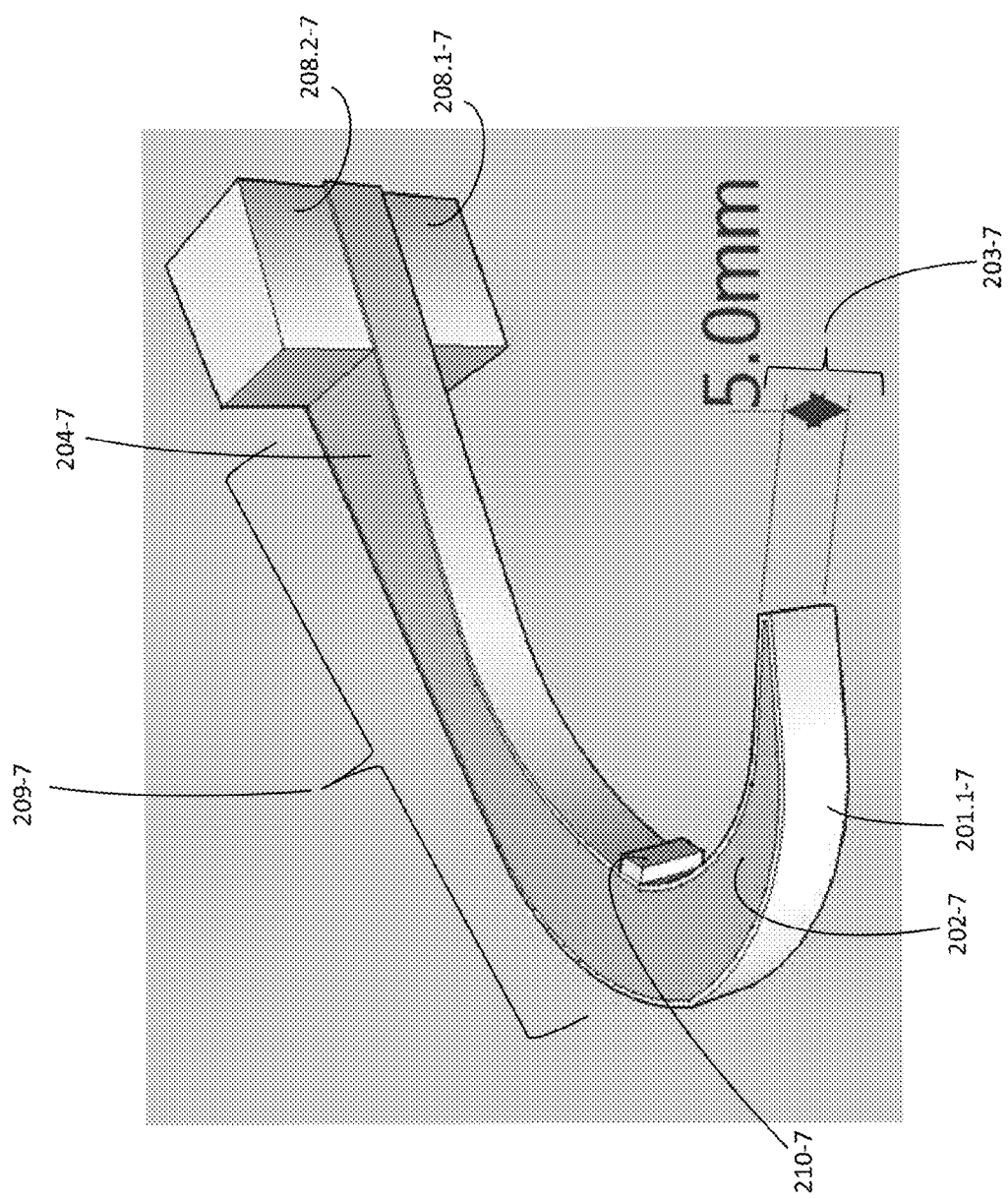
FIG. 2E is a graphical representation of another embodiment of an edge swab.

FIG. 2E shows another embodiment of an edge swab. This embodiment may be particularly useful for hard to reach substrates, for instance, the inside edge of a door handle. The handling component 209-7 is composed of a support portion 202-7 and handle portion 204-7. The support portion 202-7 underlays and creates an angled fold for the active collection component (the outer surface is shown, 201.1-7) where the active collection surface area 203-7 is the surface area around the angled fold. The width of this active collection surface area is 5 mm. In other embodiments, this width may be larger or smaller as desired. The active collection component 201.1-7 can be detachably connected to the handling component 209-7 by clips or other fittings at securing elements 208.1-7 and 208.2-7, perforations as it passes under the elements 208.1-7 and 208.2-7, or removable adhesive to any section of the handling portion 204-7. An additional securing element, 210-7 may be used to keep the active collection component connected to the handling component, and this securing element may be removable to permit detachment of the active collection component after the sample has been collected.

FIG. 3 shows another embodiment of a sample collection device. The handling component is composed of a support portion 302 and a handle portion 304. The support portion 302 underlays and supports the active collection surface area 303 of the active collection component 301. The device has a very condensed active collection surface area 303 that contacts the sample on the substrate. The width of the active collection surface area of this embodiment is about 5 mm wide. In some embodiments, the handle portion 304 may be less than 2 cm long. At least one portion of the active collection surface area 303 is removed and used in an analysis. In some embodiments, securing elements 308 (only one marked) connect the active collection component detachably via snaps, clips, or other pressurizing elements that hold the active collection component against the handling component. In some embodiments, the at least one portion may be placed into the bottom of a well of a typical 96 well reaction plate and be submerged when using volumes of about 25 uL, which is a typical volumes, for example for a PCR reaction. In some embodiments, the at least one portion of the active collection surface area is configured to fit in the bottom of a typical 96 well reaction plate and be submerged when using volumes of about 2 ul to about 50 ul. The active collection component may be compatible with PCR reaction reagents and conditions.

Figure 4:
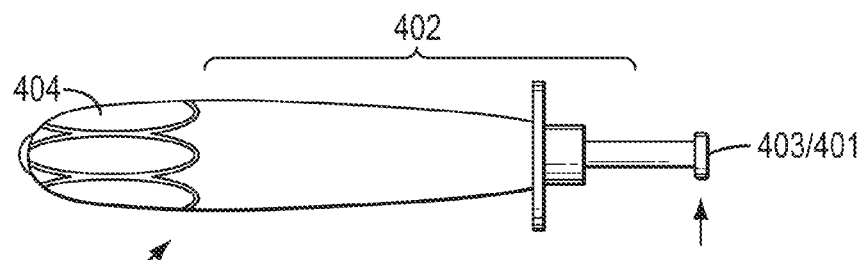
FIG. 4 is a graphical representation of an embodiment of a sample collection device having a handle and an active collection component.

FIG. 4 shows another embodiment 400 of a sample collection device. The handle portion 404 extends to a support portion 402 which underlays the active collection surface area 403 of the active collection component 401, which in this embodiment is a paper disc. The active collection component 401 is attached to the support 402 by exerting negative pressure via a suction mechanism within handle 404. The active collection surface area may be swabbed with some pressure upon a substrate to collect a sample to the active collection surface area 403. Upon releasing the negative pressure the active collection surface area 403 is detached from the handling component for analysis.

Figure 5:
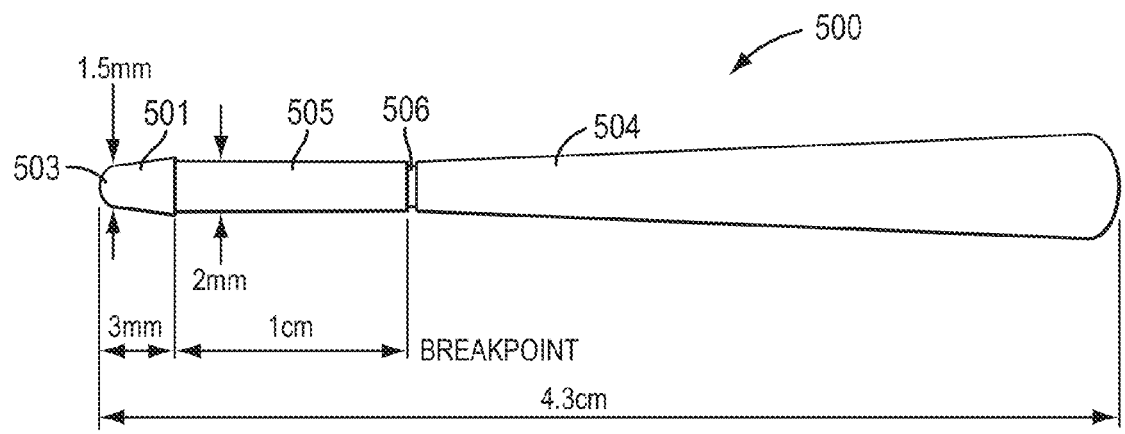
FIG. 5 is a graphical representation another embodiment of a sample collection device having a handle and an active collection component having an active surface area.

FIG. 5 shows yet another exemplary sample collection device 500. The active surface area 503 of the active collection component 501 may be swabbed on a substrate to collect a sample to the active collection surface area 503. The active collection surface area 503 may have a radius of as small as about 1.5 mm, and the active collection component 501 may have a length of about 3 mm. The active collection component may be connected via connector component 505 via a fracturable joint 506 to handle portion 504. In other embodiments, the joint 506 is not fracturable; the connector component is therefore connected directly to the handle 504. The size, shape and volume of the active collection component of the device may be configured so it may be placed into the bottom of a well of a typical 96 well reaction plate and be covered with anywhere from 2 ul to 25 ul reaction volume. The active collection component and shaft may be compatible with reaction reagents and conditions, for example, PCR reaction reagents and conditions. The active collection component 501 can be made of any material that enhances sample collection from the substrate. Exemplary materials that may be used to make the active sample collection component include, but are not limited to Nylon® fibers, cotton fibers, Whatman filter paper or any other chemically treated paper suitable to enhance concentration of the sample from the substrate to the active collection component.

In this embodiment, the active collection component containing a collected sample may be detached from the sample collection device by fracturing the fracturable joint 506 and disconnecting the at least first portion of the active collection surface area from the handle 504. Therefore, in some embodiments, the invention provides a sample collection device, having an active collection component entailing a first surface area configured to be an active collection surface area; and a handling component; where the active collection component is detachably connected to a second portion of the handling component; and where the device is configured to: a) collect a sample from at least a first surface area of a substrate to the active collection surface area; and b) permit analysis of the sample concentrated on at least a first portion of the active collection surface area.

Sample. A sample that may be collected by sample collection device described here may include a biological sample, an environmental sample, or a chemical sample. In some embodiments, the biological sample may be that of an individual, an animal, plant, fungi, bacteria or a virus. The biological sample may be a whole cell or a fragment of a cell, an intracellular component of a cell, or a biomolecule produced within or by a cell. The biomolecule may be a biosynthetic or bioproduction intermediate, metabolite or products. The biomolecule may be a protein, a glycosylated protein, a nucleic acid, a lipid, or a natural product. Any of the preceding biomolecules, cells or fragments of cells may be the substance of interest which is potentially on a substrate to be tested.

In other embodiments, the sample may be an environmental sample. This may include biological samples which are found on substrates such as furniture, buildings, pavement, and vehicles, on or in the ground or water features. An environmental sample may also be a chemical substance which may be a pollutant, toxin, agricultural trace material, radioactive material, paint, cosmetic, or fuel residue.

In yet other embodiments, the sample may be an explosives residue, including firearm residue found in the environment or forensics investigation site.

Any of these samples may be a forensics sample, food safety sample, medical outbreak sample, importation control sample for foods or other animal importation, or human identification sample.

Substrate. A substrate may be any kind of physical material from which a sample may be collected. In some embodiments, a substrate may be an item or surface in a criminal investigative scene that may have biological or chemical samples for which identification is needed, including identification of an individual leaving the sample on the substrate. In other embodiments, a substrate is a surface that may have toxins, pathogens or chemicals requiring identification. In yet other embodiments, the substrate is the skin or surface of an animal or plant requiring identification of the animal or plant species or requiring identification of pathogen, virus, parasite, or infective agent on the animal or plant. In some other embodiments, a substrate may be human or animal body parts, including a human cheek or face. A substrate may be solid or liquid. In some embodiments, fluids may be collected to identify a biological or chemical species in the fluid.

Collection Assistance Liquid. In aspects of the invention, a collection assistance liquid may be present when a sample is collected to the active collection component. A collection assistance liquid may be a solvent, a detergent, or a lysis solution.

In some embodiments, a solvent may be added to the substrate or to the active collection component as the collection of the sample to the active collection component is performed.

Solvent. Some suitable solvents that may assist with collection of a substance of interest that may potentially be present within a sample may include water, ethanol or acetonitrile. In some embodiments, the presence of one of these solvents may help to collect more of a substance of interest that may be present on a substrate. Additionally, when the substance of interest may be a large biomolecule such as a protein or nucleic acid, the use of a solvent such as water, ethanol, or acetonitrile also provide a further concentrating effect as the biomolecule as well as small molecules such as salts are collected to the active collection surface area. If a solvent is present, the smaller molecules may be further transported out of the at least first portion of the active collection surface area, while the larger biomolecule is retained within the at least first portion of the active collection surface area.

As used here, the term "detergent" is any substance that reduces the surface tension of water, and is used synonymously with the term "surfactant". In certain embodiments, the detergent can be a cationic detergent, anionic detergent, nonionic detergent, or a zwitterionic detergent. Examples of nonionic detergents include triton, such as the Triton™ X series (Triton™ X-100 t-Oct-$C_6H_4$—$(OCH_2$—$CH_2)_x$OH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™ 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant.

In some embodiments, a surfactant that substantially lacks fluorescence between 300 nm and 750 nm is used in the methods of the invention. In some embodiments provided herein, the lysis solution comprises a surfactant at a concentration that has low or no emission at the emission wavelengths of dyes or labels commonly used for detecting RNA, DNA, or proteins when in use for in situ analysis of DNA, RNA, proteins or a surrogate thereof.

In some embodiments, an effective concentration of surfactant in a lysis mixture is a concentration of surfactant at which a sample is considered fully lysed as determined by propidium iodide staining using 1% TRITON X100™ surfactant as a control. Lysis-effective concentrations of exemplary surfactants range from 0.02% or 0.05%, to 3% or more for TRITON X-114™ surfactant, from 0.1% to 5% or more for NP-40™ surfactant, and from 0.05% to 1% or to 3% for TRITON X-100™ surfactant. When a combination of surfactants is used, the concentration of each surfactant may be lowered from the cited amounts.

The lysis solution may contain an enzyme to facilitate collection of a substance of interest onto an active collection component. In certain embodiments, the lysis solution contains proteinase K. In various embodiments, proteinase K may be present in the lysis solution at about 0.8 mg/ml to about 1.5 mg/ml. In certain other embodiments the lysis solution can contain a protease enzyme. The enzyme may degrade structural proteins in order to permit extraction of biomolecules from biological cells on the substrate. The enzyme may be applied to the substrate while collection of the sample is performed, or the enzyme may be incorporated into the active collection component, such as incorporation into a gel, film, or paper. In certain embodiments herein, the lysis solution comprises a polypeptide having protease activity such as for example, proteinase K.

In lieu of, or in addition to, proteinase K, the lysis solution can comprise a serine protease such as trypsin, chymotrypsin, elastase, subtilisin, streptogrisin, thermitase, aqualysin, plasmin, cucumisin, or carboxypeptidase A, D, C, or Y; a cysteine protease such as papain, calpain, or clostripain; an acid protease such as pepsin, chymosin, or cathepsin; or a metalloprotease such as pronase, thermolysin, collagenase, dispase, an aminopeptidase or carboxypeptidase A, B, E/H, M, T, or U. Qiagen Protease (p/n 19155, Qiagen, Valencia, Calif.) is an alternative to proteinase K and can be inactivated by EDTA.

In other embodiments, the enzyme contained in the lysis solution is a pancreatic proteolytic enzyme, such as porcine pancreatic enzyme. Keratinases, that may have utility in collection of nucleic acids, include but are not limited to keratinases isolated from bacteria or fungi. Some keratinases have enhanced stabilities in the presence of detergents, surfactant, metal ions and solvents, which is useful for the methods of the present teachings. Some nonlimiting examples of a keratinase useful in the methods of the present teachings include the keratinases from *P. pastoris, B. megaterium,* and *B. licheniformis.*

In other embodiments, the lysis solution may include a surfactant to assist collection of the sample from the substrate or to assist in extracting a substance of interest from the sample once collected.

Identifier. In another aspect of the invention, the sample collection device can further comprise an identifier for associating identifying information with the sample. The identifier may aid in correlating various collected samples with the source of the sample, location of substrate collected from, and/or date of collection and may preclude sample mix-up and human error as may occur with nonsystematic sample labeling for identifying collected data and samples. In various embodiments, the identifier is alphanumeric, graphical, magnetic, or electromagnetic. In some embodiments, the identifier is a barcode. In various embodiments, the active collection component, the handling component, or both include an identifier.

In embodiments where one or more enclosures are provided, an enclosure may also include an identifier to associate the sample with the active collection component, one or more portions of the active collection surface area, and/or portions of the active collection surface area or active collection component that are being shipped, stored or archived. The identifier may be alphanumeric, graphical, magnetic, or electromagnetic. In some embodiments, the identifier is a barcode.

Kits. The invention also provides for kits. A kit may include any of the sample collection devices described here in any combination, and optionally, instructions for its use. The kit may include a collection assistance liquid, including but not limited to a solvent, a detergent or a lysis solution. The kit may further include reagents for stabilizing the sample on the active collection component for archiving or shipping. The kit may further include reagents for analysis of the sample, including but not limited to antibodies, stains, indicators, agar plates, or nucleic acid amplification reagents. The kit may contain reagents for analyses such as STR, SNP or Indel analyses.

In various embodiments, the kit further includes at least one enclosure to protect the active collection component, the handling component, or both from contamination prior to use. In further embodiments, the kit includes at least one enclosure to protect the active collection component, the at least first portion of the active collection surface area, and/or the at least second portion of the active collection surface area for shipping or archiving. The enclosure may include a frame to prevent contamination of any portion of the active collection component. Any portion of the at least one enclosure may include an identifier to associate any of the portions of the active collection component with the substrate from which the sample was obtained. In various embodiments, the identifier is alphanumeric, graphical, magnetic, or electromagnetic. In some embodiments, the identifier is a barcode.

In a further aspect, the invention provides a kit including a handling component including a support portion and a handle portion, where the handling component is configured to support an active collection component for collection of a sample, and optionally, instructions for use. In some embodiments, the support portion of the handling component tapers to a thin edge. The support portion may taper to a thin edge having a width less than about 20 mm wide and having a thickness less than about 5 mm. In other embodiments, the support portion may taper to a thin edge having a width less than about 5 mm wide and a thickness of less than about 3 mm thick. The handle portion may be less than about 20 mm long. In some embodiments, the handling component is plastic. In some embodiments, the kit further includes one or more active collection components. The active collection component may include an active collection surface area. In some embodiments, the active collection component is a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. The material for the active collection component may have a strip shape and may be of uniform width along its length. Alternatively, the material may be fabricated with a uniform width throughout its length, except at the active collection surface area supported by the tapered edge of the support portion of the handling component, where it may have a decreased width relative to the remainder of the active collection component. The kit may further include removable attachments to attach the active collection component to the handling component, selected from the group of O-rings, snaps, clips, guideholes and securing pins, and double sided tape.

Methods. Methods for collection of a sample are described which include the steps of providing a sample collection device which includes an active collection component having a first surface area configured to be an active collection surface area; a handling component; where the active collection component is detachably connected to at least one of a first or a second portion of the handling component; and where the device is configured to: a) collect a sample from at least a first surface area of a substrate to the active collection surface area; and b) permit analysis of the sample concentrated on at least a first portion of the active collection surface area; providing a substrate comprising a sample; and collecting the sample by contacting an active collection surface area of an active collection component of the sample collection device to at least a first surface area of the substrate. In some embodiments, the step of collecting the sample thereby concentrates the sample to the active collection surface area.

In some embodiments of the method for collection of a sample, the method may further include the step of detaching the active collection component from at least one of a first or a second portion of the handling component of the sample collection device. The method may further include the step of separating at least a first portion of the active collection surface area from the active collection component.

The method for collection of a sample may further include the step of providing an identifier to associate the sample collected to the active collection surface area with the substrate from which the sample was collected, where the identifier is alphanumeric, graphical, magnetic, or electromagnetic. The identifier may be a barcode.

In various embodiments of the method for collection of a sample, the method may further include the step of shipping the sample collection device including the sample to another location for archiving or testing. In other embodiments, the method may further include the step of shipping the active collection component including the sample to another location for archiving or testing.

In some embodiments of the method for collection of a sample, the sample may be a biological sample, an environmental sample, or an explosives residue sample. In some embodiments of the method, the sample may be a forensics sample.

Another method provided here is a method of identification of a substance of interest which may be present in a sample on a substrate, comprising the steps of: providing a sample collection device which includes an active collection component having a first surface area configured to be an active collection surface area; a handling component; where the active collection component is detachably connected to at least one of a first or a second portion of the handling component; and where the device is configured to: a) collect the sample from at least a first surface area of a substrate to the active collection surface area; and b) permit analysis of the sample concentrated on at least a first portion of the active collection surface area; providing a substrate comprising a sample; and collecting the sample by contacting an active collection surface area of an active collection component of the sample collection device to at least a first surface area of the substrate; and subjecting the sample to an analysis to identify the substance of interest. In various embodiments, the analysis may be at least one of a polymerase chain reaction, a DNA sequencing reaction, STR analysis, SNP analysis, or Indel analysis. In various embodiments, the analysis may provide identification of a human. In some embodiments, the step of collecting the sample to the at least first portion of the active collection surface thereby concentrates the sample from the substrate.

In some embodiments of the method for identification of the substance of interest, the method may further include the step of detaching the active collection component from at least one of the first or the second portion of the handling component of the sample collection device. The method may further include the step of separating at least a first portion of the active collection surface area from the active collection component. The method may further include the step of providing an identifier to associate the sample collected to the active collection surface area with the substrate from which the sample was collected, where the identifier is alphanumeric, graphical, magnetic, or electromagnetic. The identifier may be a barcode.

In various embodiments of the method for identification of the substance of interest, the method may further include the step of shipping the sample collection device including the sample to another location for archiving or testing. In other embodiments, the method may further include the step of shipping the active collection component including the sample to another location for archiving or testing.

In various embodiments of the method for identification of the substance of interest, the method may further include the step of sending the identity of the substance of interest to at least one of a law enforcement agency, immigration control agency, forensics investigative agency, food safety agency, public health agency, or financial services agency.

In some embodiments, the sample may contain nucleic acids, protein, subcellular fragments, secretions, or antigens of a non-human species, and the non-human species identified by the analysis is a pathogen. In some embodiments, the pathogen may be a toxin, infectious agent, or virus. The analysis identifying a pathogen may be microbiological analysis, protein analysis, or glycan analysis. In other embodiments, the sample is an environmental sample or a ballistics sample, and the analysis identifies a chemical signature of a component of the environmental or explosives residue sample. In other embodiments, the sample is an environmental sample, and the analysis identifies paint, metal, fiber, or soil composition.

Many analytical methods may be suitable to identify the substance of interest, and the methods described here are in no way limiting. If a sample contains nucleic acids, then genetic analysis may be performed. If the sample comprises nucleic acid of an individual, then the genetic analysis may identify the individual. Analysis for nucleic acid markers such as DNA markers for STRs, Indels, SNPs and combinations thereof as well as DNA sequencing methods may be performed. Reagents for amplifying a sample containing nucleic acids are readily commercially available and include primers, nucleotides, and enzymes such as a polymerase or ligase. Reagents for analyzing nucleic acids are commercially available and include such reagents as the Amp-FISTR® Identifiler® Direct PCR Amplification Kit (Applied Biosystems, Foster City, Calif.), AmpFISTR® NGM® Select PCR Amplification Kit (Applied Biosystems, Foster City, Calif.), or the PowerPlex® 18D System (Promega Corp. Madison, Wis.), which may be used in conjunction with Prep-n-Go™ Buffer (Applied Biosystems) following the manufacturer's instructions. These kits may most often be used in conjunction with detection of the markers or nucleic acid sequence identity by capillary electrophoresis, detection of the nucleic acid sequence or DNA marker may also be performed by semi-conductor sequencing, pyrophosphate sequencing, hybridization assays, and the like.

If the sample comprises nucleic acid of an animal, plant, bacteria or virus, the genetic analysis may identify the animal, plant, bacteria, virus, toxin or pathogen. The analysis may identify an animal, plant, bacteria, virus or pathogen using labeled hybridization methods, rather than sequencing analyses.

In other embodiments, analysis of proteins, biosynthetic or bioproduction intermediates, metabolites or products may be performed. The analysis may be performed using antibodies, mass spectrometry, LC/MS, or glycan analysis via GC/MS, MALDI, or electrospray. Analyses of other chemical species such as explosives residues may be accomplished via LC/MS or atomic absorption spectroscopy. Many other methods may be used and this list is by no means intended to be limiting.

Those having ordinary skill in the art will understand that many modifications, alternatives, and equivalents are possible. All such modifications, alternatives, and equivalents are intended to be encompassed herein.

EXAMPLES

The following procedures are representative of procedures that can be employed for the collection, analysis and archiving/cataloging of samples. In particular, the examples illustrate the collection and analysis of a biological sample from various substrates in the environment, but are not meant to be limiting in either type of sample nor type of substrate sample.

A sample potentially containing DNA of an individual is collected onto the active collection component of a sample collection device according to the embodiments described in FIG. 2C. The edge swab is made by wrapping a 5 mm by 80 mm filter paper strip (Whatman, cat #: 3030-6189) over a plastic handling component having a narrow active collection surface are supported by a protuding portion of the support portion of the handling component of the swab. The active swabbing area, the active collection surface area, has a dimension of about 1 mm by about 5 mm width.

After swabbing the substrate the active collection component strip is detached from the handling component and two 2 mm diameter punches are generated from the active swabbing area using a Harris Uni-Core punch. Alternatively punches can be generated automatically, for example, by using a BSD punching instrument. Punches are then placed directly into a well of a 96-well PCR plate. 7 ul PCR reaction mix, which includes GlobalFiler® Master Mix and Identifier® Direct primer mix, is added to the well containing the paper punches. The thermo cycling conditions are 95° C./1 m, 29 cycles of (94° C./10s, 59° C./90sec), 60° C./10 min and 4° C.-hold. After thermal cycling 1 uL PCR product from each sample is mixed with GeneScan®500 size standard and deionized formamide and analyzed using a ABI 3130xI capillary electrophoresis instrument using the following conditions: Oven: 60° C., Prerun: 15 kV, 180s, Injection: 3 kV, 10s, Run: 15 kV, 1500s, Capillary length: 36 cm, Separation polymer: POP4™ polymer and Dye set: G5. The resulting STR electropherogram is analyzed using GeneMapper® ID-X software (Applied Biosystems).

The alleles for each electropherogram using primers provided by the Identifiler Direct® PCR reaction mix are as follows:

First panel, from left to right: D8S1179; D21511; D7S820; and CSF1PO. Second panel, from left to right: D3S1358; THO1; D135317; D165539; and D2S1338. Third panel: D195433; MA; TPOS; and D18551. Fourth panel, from left to right: Amelogenin, D5S818, and FGA.

Example 1

Figure 6C:
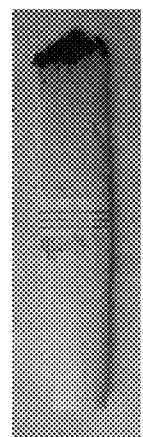
FIG. 6 is a graphical representation of the substrates contacted by an edge swab, providing samples according to the Examples.
Figure 6F:
Figure 6B:
Figure 6E:
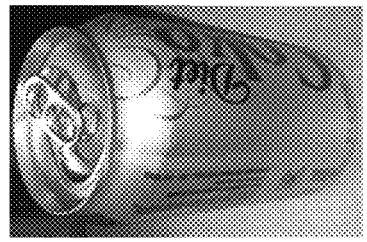
Figure 6A:

An edge swab as shown in FIG. 2C is used to collect a biological sample from a coffee mug substrate, as shown in FIG. 6A.

The sample is processed as described in the general conditions described above and the amplified nucleic acids are analyzed as described above to generate a STR profile of an individual who deposited the sample on the coffee mug. As can be seen in FIGS. 7A-D, a full profile is obtained, and identification of the individual is definitively made.

Example 2

An edge swab as shown in FIG. 2C is used to collect a biological sample from a computer keyboard substrate, as shown in FIG. 6B.

The sample is processed as described in the general conditions described above and the amplified nucleic acids are analyzed as described above to generate a STR profile of an individual who deposited the sample on the coffee mug. As can be seen in FIGS. 8A-D, a full profile is obtained, and identification of the individual is definitively made.

Example 3

An edge swab as shown in FIG. 2C is used to collect a biological sample from a handled cigarette remnant substrate, as shown in FIG. 6C.

The sample is processed as described in the general conditions described above and the amplified nucleic acids are analyzed as described above to generate a STR profile of an individual who deposited the sample on the coffee mug. As can be seen in FIGS. 9A-D, a full profile is obtained, and identification of the individual is definitively made.

Example 4

Figure 6D:
Figure 7A:
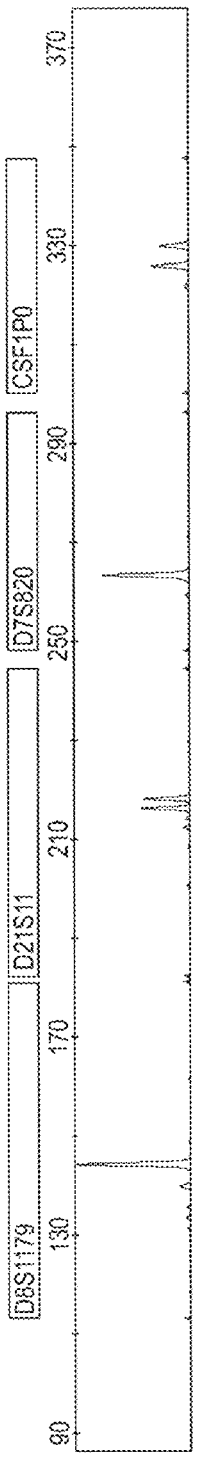
FIG. 7A-D is a graphical representation of a STR analysis obtained from an individual according to the devices and methods of the invention.
Figure 7B:
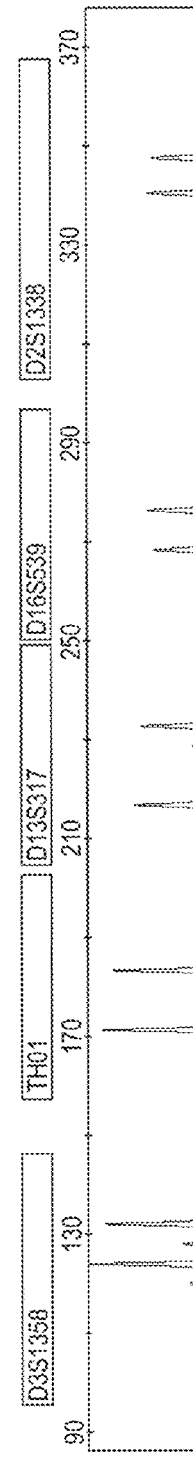
Figure 7C:
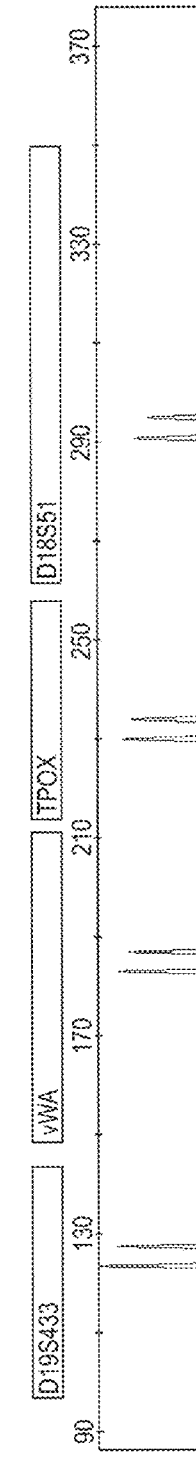
Figure 7D:
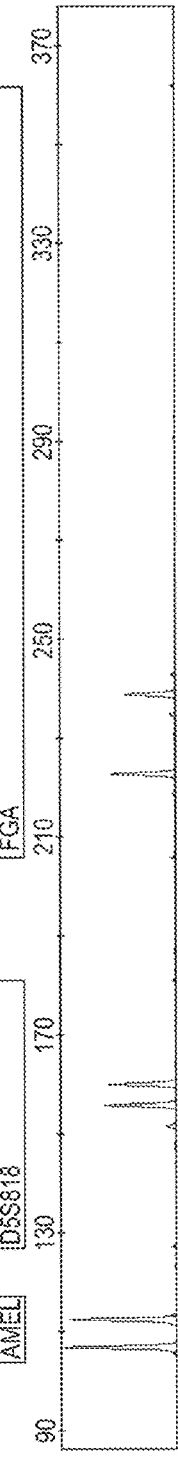
Figure 8A:
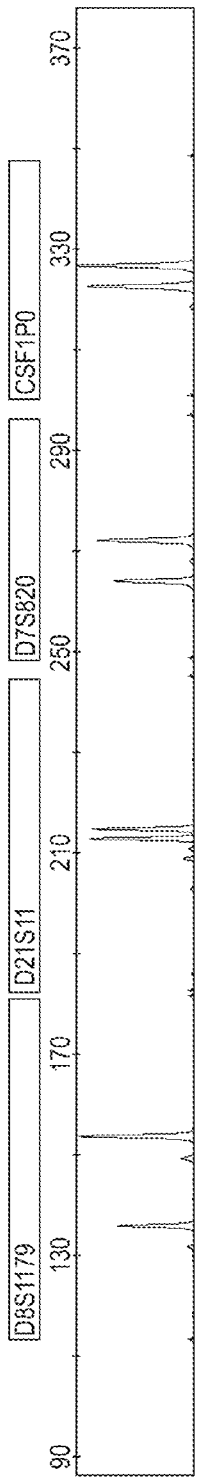
FIG. 8A-D is a graphical representation of a STR analysis obtained from an individual according to the devices and methods of the invention.
Figure 8B:
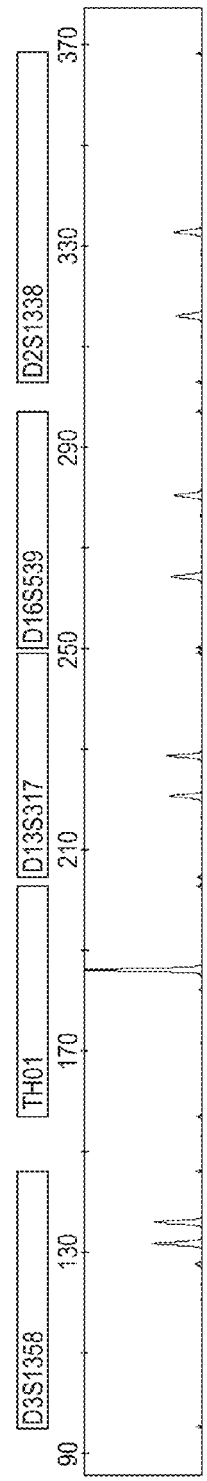
Figure 8C:
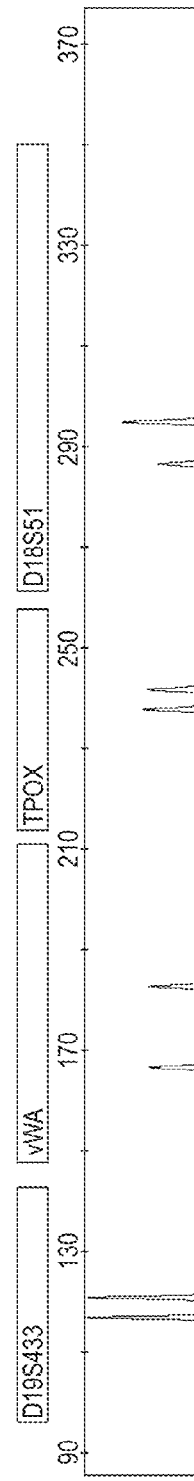
Figure 8D:
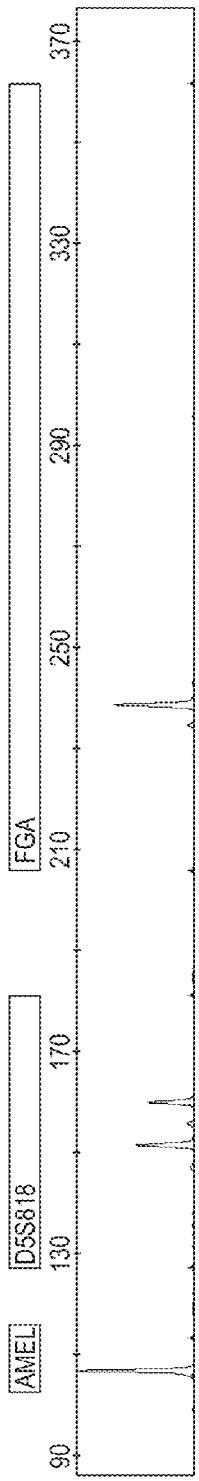
Figure 9A:
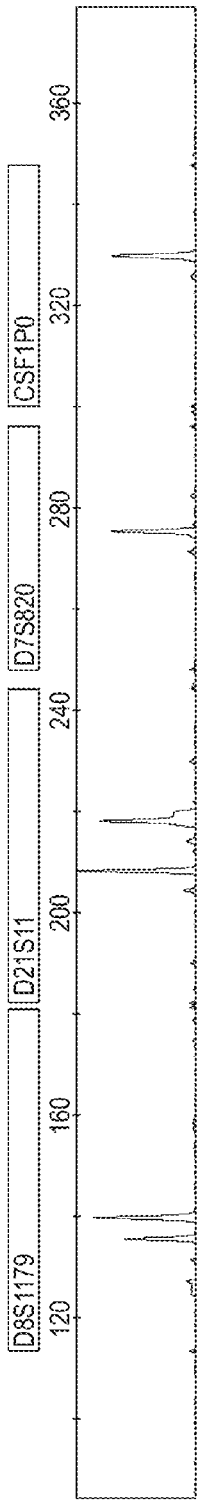
FIG. 9A-D is a graphical representation of a STR analysis obtained from an individual according to the devices and methods of the invention.
Figure 9B:
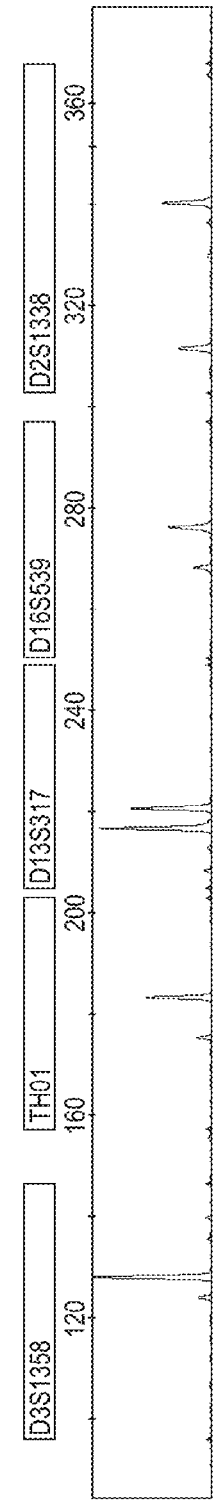
Figure 9C:
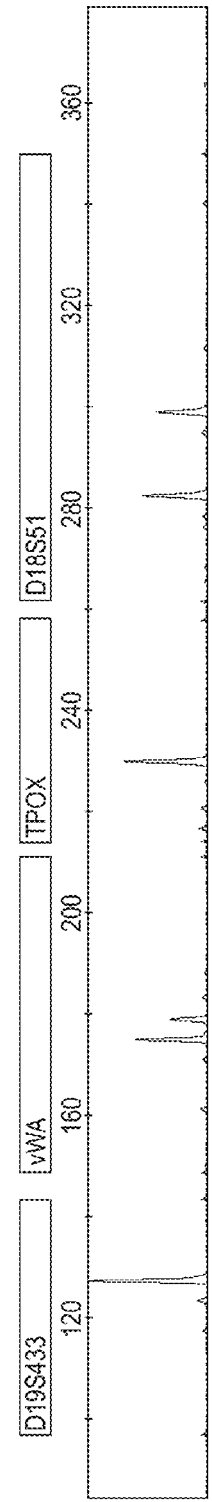
Figure 9D:
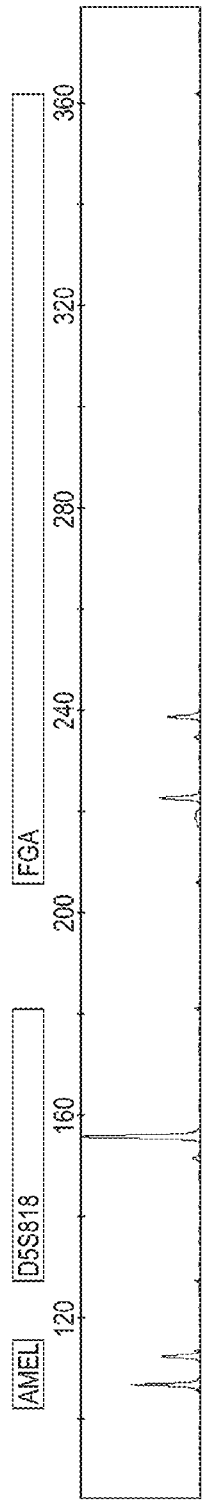
Figure 10A:
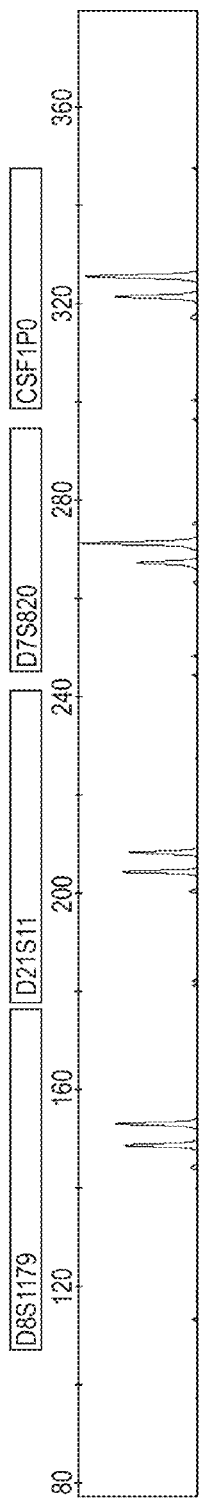
FIG. 10A-D is a graphical representation of a STR analysis obtained from an individual according to the devices and methods of the invention.
Figure 10B:
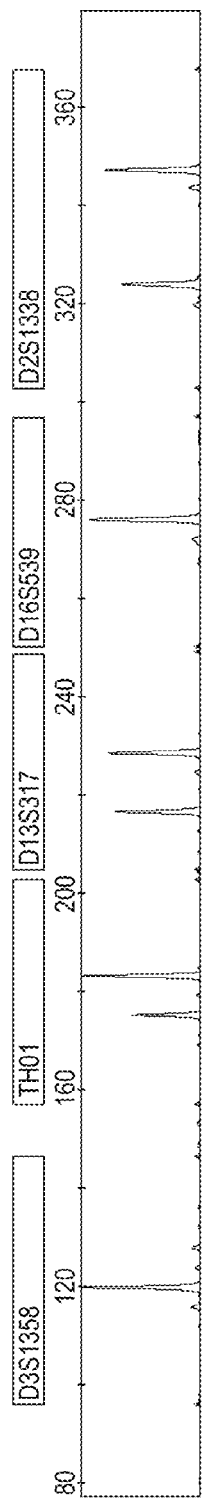
Figure 10C:
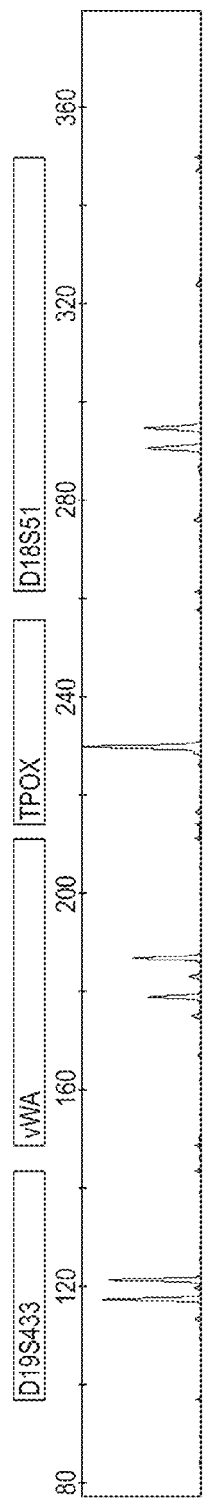
Figure 10D:
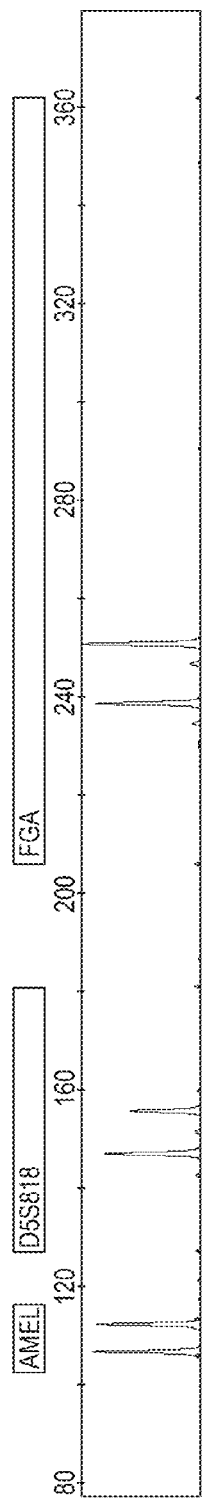
Figure 11A:
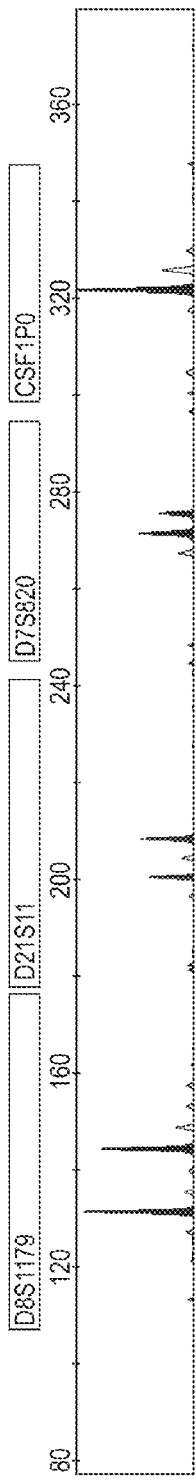
FIG. 11A-D is a graphical representation of a STR analysis obtained from an individual according to the devices and methods of the invention.
Figure 11B:
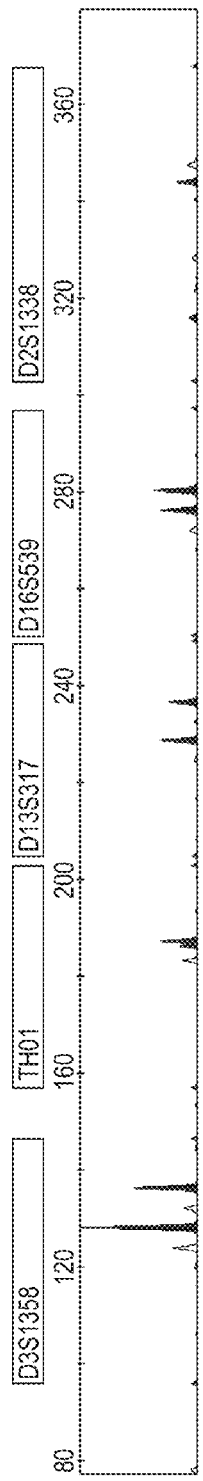
Figure 11C:
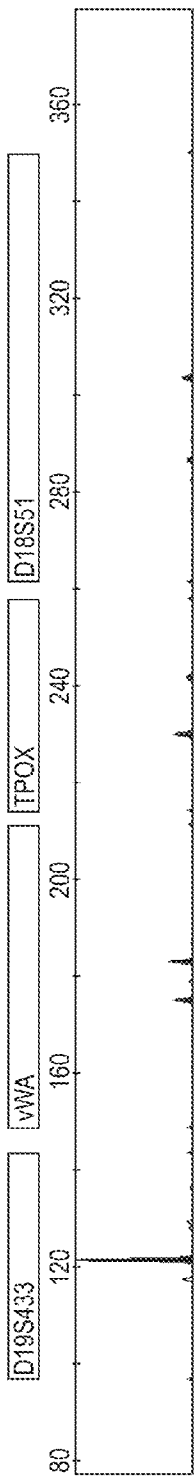
Figure 11D:
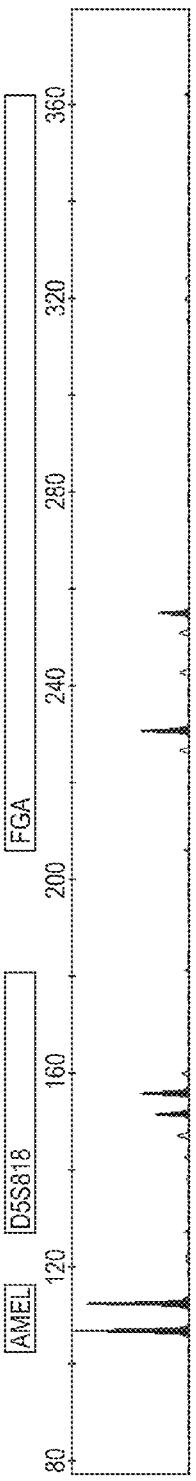
Figure 12A:
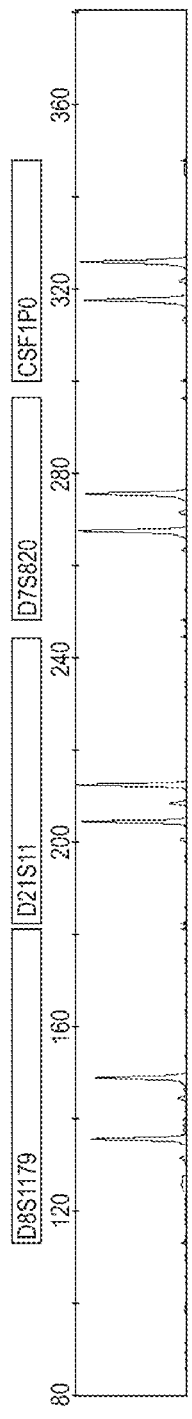
FIG. 12A-D is a graphical representation of a STR analysis obtained from an individual according to the devices and methods of the invention.
Figure 12B:
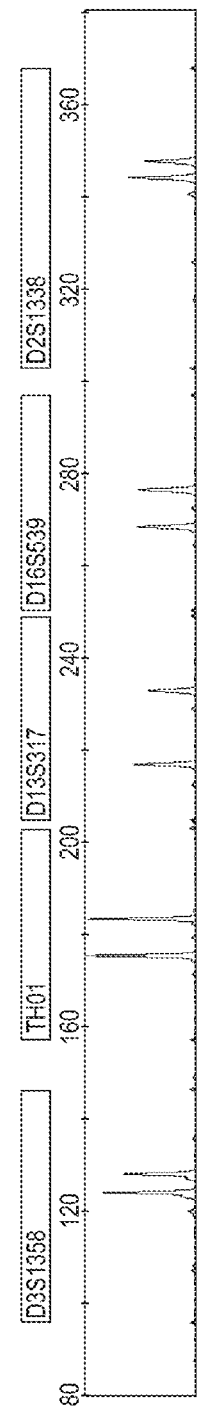
Figure 12C:
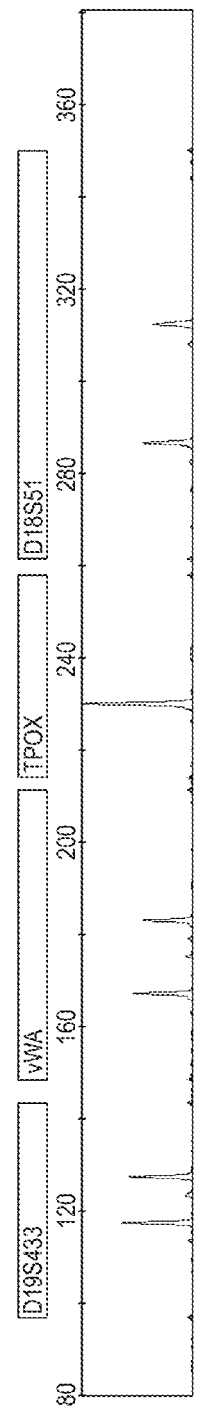
Figure 12D:
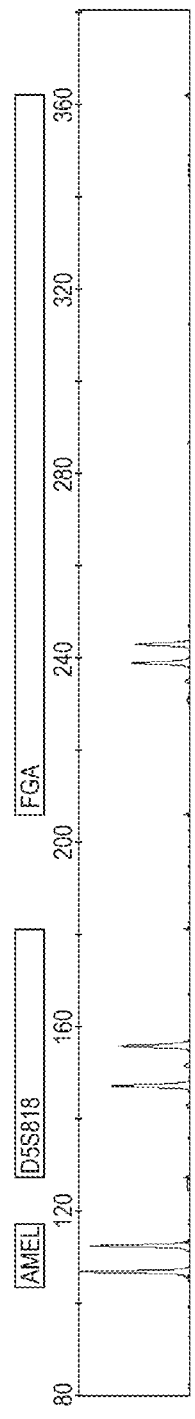

An edge swab as shown in FIG. 2C is used to collect a biological sample from the finger region of a previously worn laboratory glove substrate, as shown in FIG. 6D.

The sample is processed as described in the general conditions described above and the amplified nucleic acids are analyzed as described above to generate a STR profile of an individual who deposited the sample on the coffee mug. As can be seen in FIGS. 10A-D, a full profile is obtained, and identification of the individual is definitively made.

Example 5

An edge swab as shown in FIG. 2C is used to collect a biological sample from the finger region of a previously handled soda can substrate, as shown in FIG. 6E.

The sample is processed as described in the general conditions described above and the amplified nucleic acids are analyzed as described above to generate a STR profile of an individual who deposited the sample on the coffee mug. As can be seen in FIGS. 11A-D, a full profile is obtained, and identification of the individual is definitively made.

Example 6

An edge swab as shown in FIG. 2C is used to collect a biological sample from the collar region of a previously worn shirt substrate, as shown in FIG. 6F.

The sample is processed as described in the general conditions described above and the amplified nucleic acids are analyzed as described above to generate a STR profile of an individual who deposited the sample on the coffee mug. As can be seen in FIGS. 12A-D, a full profile is obtained, and identification of the individual is definitively made.

While the foregoing specification teaches the principles of the present invention, with examples provided for the purpose of illustration, it will be appreciated by one skilled in the art from reading this disclosure that various changes in form and detail can be made without departing from the spirit and scope of the invention.

What is claimed:

1. A sample collection device comprising:
an active collection component comprising a first surface area configured to be an active collection surface area, wherein the active collection surface area is configured to be the surface area encompassing an exterior edge of an angled fold of the active collection component and wherein the angled fold is formed over the first portion of a handling component;
wherein the active collection component is detachably connected to at least one of a first or a second portion of the handling component; and
wherein the device is configured to: a) collect a sample from at least a first surface area of a substrate to the active collection surface area; and b) permit analysis of the sample concentrated on at least a first portion of the active collection surface area.

2. The sample collection device of claim 1, wherein the active collection surface area is configured to provide at least a second portion of the active collection surface area for archiving.

3. The sample collection device of claim 1, wherein the active collection component comprises fibrous material.

4. The sample collection device of claim 3, wherein the fibrous material comprises natural fibers, synthetic polymeric fibers or a combination thereof.

5. The sample collection device of claim 3, wherein the fibrous material is cotton, or paper, and optionally, wherein the fibrous material is chemically treated.

6. The sample collection device of claim 1, wherein the first portion of the handling component further comprises a layer of absorbent material underlying the active collection component.

7. The sample collection device of claim 1 wherein the first portion of the handling component comprises a stiffening support for the active collection component.

8. The sample collection device of claim 1, wherein a length of the active collection component along the angled fold is about 20mm or less.

9. The sample collection device of claim 1, wherein the exterior edge of the angled fold forms an acute angle.

10. The sample collection device of claim 1, wherein the active collection surface area is at least about 50% smaller than the at least first surface area of the substrate.

11. The sample collection device of claim 1, wherein the collecting of the sample to the at least first portion of the active collection surface thereby concentrates the sample from the substrate.

12. The sample collection device of claim 1, wherein the at least first portion of the active collection surface area is configured to fit within a reaction volume of about 2ul to about 100ul.

13. The sample collection device of claim 1, wherein the active collection component, the handling component, or both comprise an identifier to associate the sample with the substrate from which the sample was collected, wherein the identifier is alphanumeric, graphical, magnetic, or electromagnetic.

* * * * *